(12) United States Patent
Shraiki et al.

(10) Patent No.: US 11,793,677 B2
(45) Date of Patent: Oct. 24, 2023

(54) PATIENT INTERFACE SYSTEM, METHOD FOR COUPLING A PATIENT INTERFACE TO A PATIENT INTERFACE HOLDER, PATIENT INTERFACE, AND PATIENT INTERFACE HOLDER

(71) Applicant: SCHWIND EYE-TECH-SOLUTIONS GMBH, Kleinostheim (DE)

(72) Inventors: Mario Shraiki, Stockstadt (DE); Nico Triefenbach, Mainaschaff (DE); Thomas Wendler, Stockstadt (DE); Stefan Troller, Sissach (CH); Amir Feriani, Auvernier (CH); Michel Saint-Ghislain, Düdingen (CH)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 0 days.

(21) Appl. No.: 16/753,706

(22) PCT Filed: Oct. 5, 2018

(86) PCT No.: PCT/EP2018/077136
§ 371 (c)(1),
(2) Date: Apr. 3, 2020

(87) PCT Pub. No.: WO2019/068867
PCT Pub. Date: Apr. 11, 2019

(65) Prior Publication Data
US 2020/0268553 A1 Aug. 27, 2020

(30) Foreign Application Priority Data
Oct. 6, 2017 (DE) .................... 10 2017 123 300.8

(51) Int. Cl.
*A61F 9/009* (2006.01)

(52) U.S. Cl.
CPC .................................. *A61F 9/009* (2013.01)

(58) Field of Classification Search
CPC .......................... A61F 9/009; A61F 9/00825
See application file for complete search history.

(56) References Cited

U.S. PATENT DOCUMENTS 8,753,321 B2 * 6/2014 Mrochen ................. A61F 9/013
604/294
2006/0192921 A1 8/2006 Loesel et al.
(Continued)

FOREIGN PATENT DOCUMENTS

DE 10 2006 053 582 A1 5/2008
DE 102006053582 A1 * 5/2008 ............ A61M 39/08
(Continued)

OTHER PUBLICATIONS

International Search Report dated Feb. 11, 2019 in corresponding International Patent Application No. PCT/EP2018/077136.
(Continued)

Primary Examiner — Lynsey C Eiseman
Assistant Examiner — Ranjani Mari Sundaresan
(74) Attorney, Agent, or Firm — MEDLER FERRO WOODHOUSE & MILLS PLLC

(57) ABSTRACT

A patient interface system for positioning a patient's eye relative to a laser device for laser surgery is disclosed that includes a patient interface for coupling to the patient's eye, and a patient interface holder for arranging the patient interface on the laser device. The patient interface holder has a suction duct for connecting to a suction device, and the patient interface has a fluid-conducting device that couples to the patient interface holder, and when in the coupled state, together form a fluid path which fluidically couples the suction duct to the patient interface in order to hold a first positioning device of the patient interface against the (Continued)

patient's eye by a relative negative pressure generated by the suction device. A method is disclosed for coupling a patient interface to a patient interface holder, and a patient interface. A patient interface holder is also disclosed.

14 Claims, 14 Drawing Sheets

(56) References Cited

U.S. PATENT DOCUMENTS

| | | | |
|---|---|---|---|
| 2008/0114314 A1 | 5/2008 | Muehlhoff et al. | |
| 2017/0281404 A1* | 10/2017 | Wang | A61F 9/009 |
| 2017/0281407 A1 | 10/2017 | Garcia et al. | |

FOREIGN PATENT DOCUMENTS

| | | | |
|---|---|---|---|
| EP | 2 133 048 A1 | 12/2009 | |
| EP | 3 167 853 A1 | 5/2017 | |
| EP | 3167853 A1 * | 5/2017 | A61F 9/009 |
| WO | WO-2016148754 A1 * | 9/2016 | A61F 9/009 |

OTHER PUBLICATIONS

German Search Report dated Jun. 7, 2018 in corresponding German Patent Application No. 10 2017 123 300.8.

\* cited by examiner

PATIENT INTERFACE SYSTEM, METHOD FOR COUPLING A PATIENT INTERFACE TO A PATIENT INTERFACE HOLDER, PATIENT INTERFACE, AND PATIENT INTERFACE HOLDER

FIELD

The invention relates to a patient interface system for positioning a patient's eye relative to a laser device for laser surgery. Furthermore, the invention relates to a method for coupling a patient interface to a patient interface holder of such a patient interface system as well as to a patient interface and a patient interface holder for such a patient interface system.

BACKGROUND

Such a patient interface system can for example be employed in the laser-surgical treatment of a human or animal eye. Therein, the patient interface system serves for positioning and coupling the patient's eye to a laser device, which generates the laser radiation for the treatment of the patient's eye. Corresponding laser devices for example comprise a basic apparatus with a laser source for generating pulsed laser radiation, for example nano-, femto- or picosecond laser pulses, as well as an application head, which is coupled to the patient's eye via the patient interface system for treatment. The patient interface system is usually arranged between the patient's eye and a focusing system of the laser device. A fixed coupling is required to keep the distance between the laser source and its focusing system, respectively, and the patient's eye constant in order that the laser-surgical treatment can be performed with the required high precision and the laser beam can be precisely directed to the tissue of the patient's eye to be treated, for example to the cornea.

A generic patient interface system includes a patient interface for coupling to the patient's eye and a patient interface holder for arrangement of the patient interface on the laser device. Therein, the patient interface includes a first positioning device for abutting the patient interface on the patient's eye and a second positioning device for positioning the patient interface relative to the patient interface holder. The patient interface holder in turn includes a holding device, by means of which the patient interface can be reversibly coupled to the patient interface holder. In the coupled or mounted state, thus, the patient interface is coupled to the patient's eye at the one end and to the patient interface holder at the other end, while the patient interface holder in turn is coupled to the laser device such that a correct orientation between the patient's eye and the laser source is ensured.

The coupling of the patient interface to the patient's eye is usually effected by negative pressure and a suction ring fitted onto the cornea. The suction ring is the most frequent approach of fixing, but there are also other known solutions.

The circumstance is to be regarded as disadvantageous in the known patient interface system that the suction ring has to be positioned and actuated in addition to the other assemblies of the patient interface system, which considerably aggravates the preparation and performance of a laser-surgical treatment. This can also be problematic with regard to the high safety requirements in such treatment procedures.

SUMMARY

It is the object of the present invention to provide a patient interface system, the patient interface of which can be more easily handled and more safely attached to a patient's eye. A further object of the invention is in providing a method for more easily and more safely coupling a patient interface to a patient interface holder of such a patient interface system. Finally, further objects of the invention are in providing a corresponding patient interface and a corresponding patient interface holder for such a patient interface system.

According to the invention, the objects are solved by a patient interface system, by a method for coupling a patient interface to a patient interface holder of a patient interface system, a patient interface and a patient interface holder as respectively described herein. Advantageous configurations with convenient developments of the invention are specified in the respective claims, wherein advantageous configurations of each inventive aspect are to be regarded as advantageous configurations of the respectively other inventive aspects.

A first aspect of the invention relates to a patient interface system for positioning a patient's eye relative to a laser device for laser surgery, including a patient interface for coupling to the patient's eye and a patient interface holder for arrangement of the patient interface on the laser device, wherein the patient interface comprises a first positioning device for abutment of the patient interface on the patient's eye and the patient interface holder includes a holding device, by means of which the patient interface can be reversibly coupled to the patient interface holder. According to the invention, it is provided that the patient interface holder comprises a suction duct connectable to a suction device and the patient interface comprises a fluid-conducting device, wherein the patient interface holder and the fluid-conducting device of the patient interface together form a fluid path in the coupled state, which fluidically couples the suction duct to a suction opening of the patient interface in the region of the first positioning device to hold the first positioning device in abutment on the patient's eye by a relative negative pressure generated by means of the suction device. In other words, it is provided according to the invention that a fluidic coupling is also effected together with the mechanic coupling of patient interface and patient interface holder, which can be used for abutting and for holding the patient's eye on the patient interface. Hereby, a user of the patient interface system according to the invention has to couple only two assemblies, namely the patient interface and the patient interface holder, to accomplish both a mechanic coupling of the patient interface and the patient interface holder for positioning the patient's eye relative to the laser device and a connection of the patient interface to a suction device via the patient interface holder without additional manual movements or working steps, to abut the patient's eye on the first positioning device and to hold it thereon, respectively, by negative pressure. Hereby, the patient interface system can be more easily and more safely handled. Preferably, the fluid path commonly formed in the coupled state extends separately to a passage channel of the patient interface system for a laser beam of a laser device and outside of such a passage channel of the patient interface system for a laser beam of a laser device, respectively, since an impairment of an optical path and thereby potential interferences during a surgical intervention are hereby particularly reliably prevented. The passage channel for the laser beam can for example be formed by a suction cup part or be arranged within a suction cup part of the patient interface, while the fluid path is formed or arranged separated hereof.

In an advantageous configuration of the invention, it is provided that the suction duct of the patient interface holder includes a male connector, which engages with a corresponding female fitting of the patient interface in the coupled state. Hereby, the simple and reliable fluidic coupling can be achieved on the one hand, the contamination risk in the connection region of patient interface and patient interface holder is advantageously reduced on the other hand. In the time between unpacking and inserting the patient interface into the patient interface holder, the patient interface is exposed to the environment and thereby possible contaminations for a short time. Contaminations in the region of the fluidic coupling can impair the tightness of the fluidic coupling and disturb the laser-surgical treatment in the worst case. In that the patient interface comprises a female fitting with internal contact surfaces, the risk of contamination is considerably reduced compared to a male fitting.

In a further advantageous configuration of the invention, it is provided that the female fitting comprises an inner cone, in which a corresponding outer cone of the male connector is arranged in the coupled state. Hereby, a simple and gas-tight coupling in the manner of a Luer system can be achieved.

In a further advantageous configuration of the invention, it is provided that the outer cone and/or the inner cone have a contact angle between 8° and 20° according to amount. In other words, it is provided that the outer cone has an increasing outer diameter with a contact angle of 8°, 9°, 10°, 11°, 12°, 13°, 14°, 15°, 16°, 17°, 18°, 19° or 20° at least in the connection region with the inner cone in introduction direction into the inner cone, and/or that the inner cone has a decreasing inner diameter with a corresponding contact angle between 8° and 20° according to amount in introduction direction of the outer cone. For example, the outer cone can have a contact angle of 12° and the inner cone can have a contact angle of −12°. This allows simple and self-centering introduction and withdrawal of the outer cone into or from the inner cone and ensures a gas-tight connection.

In a further advantageous configuration of the invention, it is provided that the male connector is formed angled, whereby the connection of a negative pressure hose is facilitated in certain configurations. Furthermore, an angled configuration allows simpler force application on the connector in introduction direction to ensure a secure abutment on the female fitting. Alternatively or additionally, it is provided that the male connector is arranged in a groove of the patient interface holder and/or applied with force by a spring-loaded engaging element. This ensures reliable support of the male connector on the patient interface holder as well as secure abutment on the female fitting, whereby a correspondingly reliable and gas-tight coupling is achieved.

In a further advantageous configuration of the invention, it is provided that the fluid-conducting device of the patient interface includes at least one filter element. Hereby, contaminations occurring in the fluid path can be reliably intercepted, whereby disturbances of the laser-surgical treatment can be avoided.

In a further advantageous configuration of the invention, it is provided that the fluid-conducting device of the patient interface includes at least one collecting container. Hereby, contaminations occurring in the fluid path can be retained and collected.

In a further advantageous configuration of the invention, it is provided that the collecting container is inserted into a corresponding mounting opening of the patient interface. Hereby, the collecting container can be produced as a separate component and connected to the patient interface. By the multi-part construction of the patient interface, complex geometries can be more easily produced. Moreover, different component types can be combined as needed. For example, differently sized collecting containers can be provided and connected to the patient interface as needed. Alternatively or additionally, it is provided that the collecting container has a volume of at least 80 mm$^3$, thus for example of 80 mm$^3$, 85 mm$^3$, 90 mm$^3$, 95 mm$^3$, 100 mm$^3$, 105 mm$^3$, 110 mm$^3$, 115 mm$^3$, 120 mm$^3$, 125 mm$^3$, 130 mm$^3$, 135 mm$^3$, 140 mm$^3$, 145 mm$^3$, 150 mm$^3$ or more. Thereby, a sufficiently large safety buffer can be provided, to reliably collect also unexpected amounts of contaminations. A volume of 120 mm$^3$ or more is for example usually sufficient for approximately five laser-surgical treatments and thereby offers a correspondingly good safety buffer.

In a further advantageous configuration of the invention, it is provided that the filter element is arranged in a mounting opening of the collecting container. Hereby, contaminations intercepted by the filter element can be directly collected in the collecting container such that the risk of occlusions of the fluid path is minimized.

In a further advantageous configuration of the invention, it is provided that the fluid-conducting device includes a negative pressure hose. Within the scope of the present disclosure, a hose is understood by a negative pressure hose, which does not collapse and block the fluid path upon applying a negative pressure reduced with respect to a normal external pressure of about 1 bar. With the aid of the negative pressure hose, the fluid path can be particularly flexibly defined such that a corresponding flexible configuration of the patient interface is also possible.

In a further advantageous configuration of the invention, it is provided that the collecting container includes a fitting, in which a first end region of the negative pressure hose is arranged. This represents a simple possibility of attaching the negative pressure hose. In a configuration, the negative pressure hose can be adhered into the fitting to ensure a reliable and gas-tight attachment.

In a further advantageous configuration of the invention, it is provided that the fluid-conducting device includes a fitting, in which a second end region of the negative pressure hose is arranged, and which opens into the suction opening. Hereby, the negative pressure generated by the suction device can be immediately conducted to the suction opening and thereby into the vicinity of the patient's eye via the negative pressure hose, whereby a correspondingly reliable abutment of the patient's eye can be ensured.

In a further advantageous configuration of the invention, it is provided that at least one fitting comprises a mounting duct, in which the negative pressure hose is arranged in certain areas, wherein the mounting duct has a continuously and/or gradually decreasing inner diameter at least in certain areas along a mounting direction starting from an introduction opening, the inner diameter of which at least corresponds to an outer diameter of the negative pressure hose. This allows particularly simple and reliable fixing and positioning of the negative pressure hose.

A second aspect of the invention relates to a method for coupling a patient interface of a patient interface system according to the first inventive aspect to a patient interface holder of a patient interface system according to the first inventive aspect, in which the patient interface is moved relative to the patient interface holder until the suction duct of the patient interface holder and the fluid-conducting device of the patient interface are fluidically coupled and together form a fluid path, which fluidically couples the suction duct to the suction opening of the patient interface in the region of the first positioning device to hold the first positioning device in abutment on the patient's eye by a relative negative pressure generated by means of the suction device. In other words, it is provided according to the invention that a fluidic coupling is also performed together with the mechanical coupling of patient interface and patient interface holder, which can be used for abutting and for holding the patient's eye on the patient interface. Hereby, a user of the patient interface system according to the invention has to couple only two assemblies, namely the patient interface and the patient interface holder, to accomplish both a mechanical coupling of the patient interface and the patient interface holder for positioning the patient's eye relative to the laser device and a connection of the patient interface to a suction device via the patient interface holder without additional manual movements or working steps, to abut the patient's eye on the first positioning device and to hold it thereon, respectively, by negative pressure. Hereby, the patient interface system can be more easily and more safely handled. Further features and the advantages thereof can be taken from the descriptions of the first inventive aspect, wherein advantageous configurations of the first inventive aspect are to be regarded as advantageous configurations of the second inventive aspect and vice versa.

A third aspect of the invention relates to a patient interface for a patient interface system according to the first inventive aspect, wherein the patient interface comprises a fluid-conducting device, which forms a fluid path together with a suction duct of the patient interface holder connectable to a suction device in the coupled state with the patient interface holder of the patient interface system, which fluidically couples the suction duct to a suction opening of the patient interface in the region of the first positioning device to hold the first positioning device of the patient interface in abutment on the patient's eye by means of a relative negative pressure generated by means of the suction device. Thereby, the patient interface according to the invention allows also producing a fluidic coupling besides a mechanical coupling to the patient interface holder in one step in cooperation with the patient interface holder, whereby the patient interface can be more easily handled and more safely attached to a patient's eye. Further features and the advantages thereof can be taken from the descriptions of the first and the second inventive aspect, wherein advantageous configurations of the first and the second inventive aspect are to be regarded as advantageous configurations of the third inventive aspect and vice versa.

A fourth aspect of the invention relates to a patient interface holder for a patient interface system according to the first inventive aspect, wherein the patient interface holder comprises a suction duct connectable to a suction device, wherein the suction duct and the fluid-conducting device of the patient interface together form a fluid path in the coupled state, which fluidically couples the suction duct of the patient interface to a suction opening of the patient interface in the region of the first positioning device to hold the first positioning device of the patient interface in abutment on the patient's eye by a relative negative pressure generated by means of the suction device. Thereby, the patient interface holder according to the invention allows producing also a fluidic coupling besides a mechanical coupling to the patient interface in one step in cooperation with the patient interface, whereby the patient interface can be more easily handled and more safely attached to a patient's eye. Further features and the advantages thereof can be taken from the descriptions of the first, the second and the third inventive aspect, wherein advantageous configurations of the first, the second and the third inventive aspect are to be regarded as advantageous configurations of the fourth inventive aspect and vice versa.

A further aspect of the invention relates to a method for preparing and/or performing a laser-surgical treatment procedure on a patient's eye, in which a patient interface system according to the first inventive aspect is provided, the patient interface is abutted on a patient's eye by means of the first positioning device, the patient interface holder is fixed to the laser device and the patient interface is reversibly coupled to the patient interface holder by means of the holding device of the patient interface holder and positioned relative to the patient interface holder by means of the second positioning device, wherein the patient interface holder comprises a suction duct connectable or connected to a suction device and the patient interface comprises a fluid-conducting device, and wherein the patient interface holder and the fluid-conducting device of the patient interface together form a fluid path in the coupled state, which fluidically couples the suction duct to a suction opening of the patient interface in the region of the first positioning device to hold the first positioning device in abutment on the patient's eye by a relative negative pressure generated by means of the suction device. Hereby, the patient interface system can be more easily handled and more safely attached to a patient's eye, whereby the laser-surgical treatment procedure can be correspondingly simpler and more safely performed.

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

DETAILED DESCRIPTION

Figure 1:
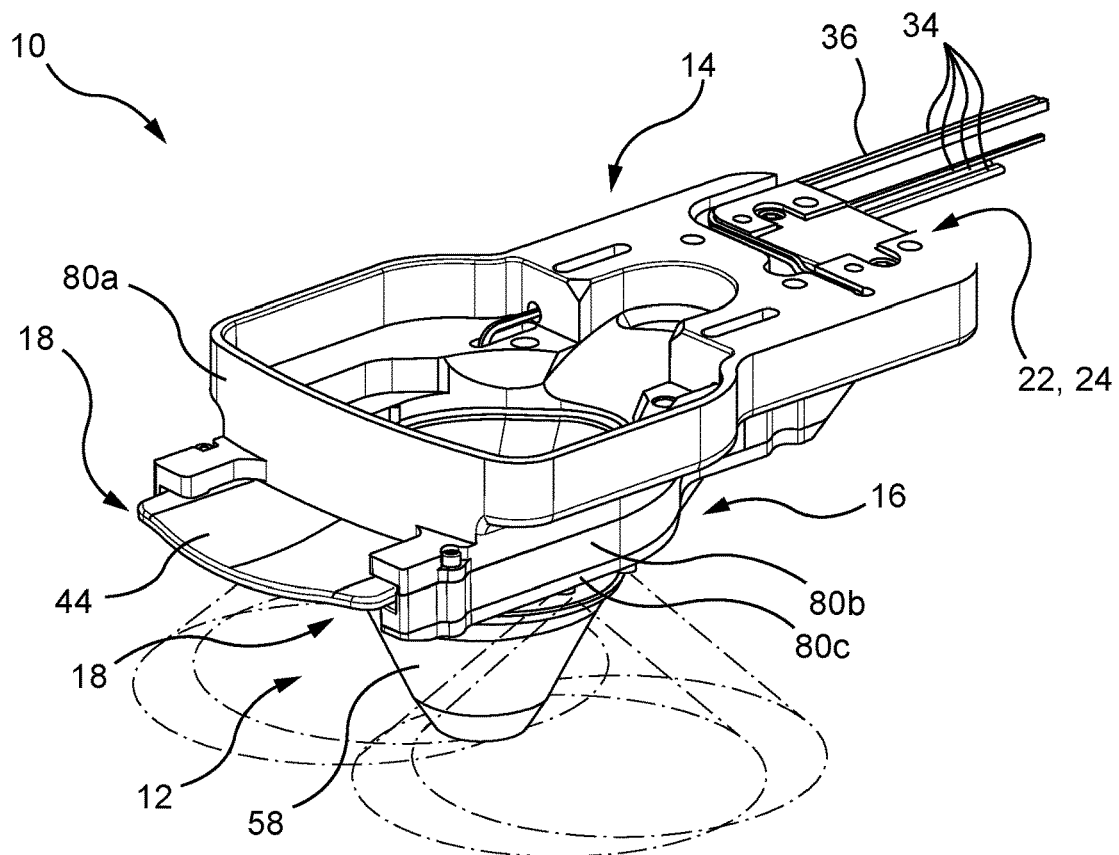
FIG. 1 is a schematic perspective view of a patient interface system according to the invention according to a first embodiment.
Figure 2:
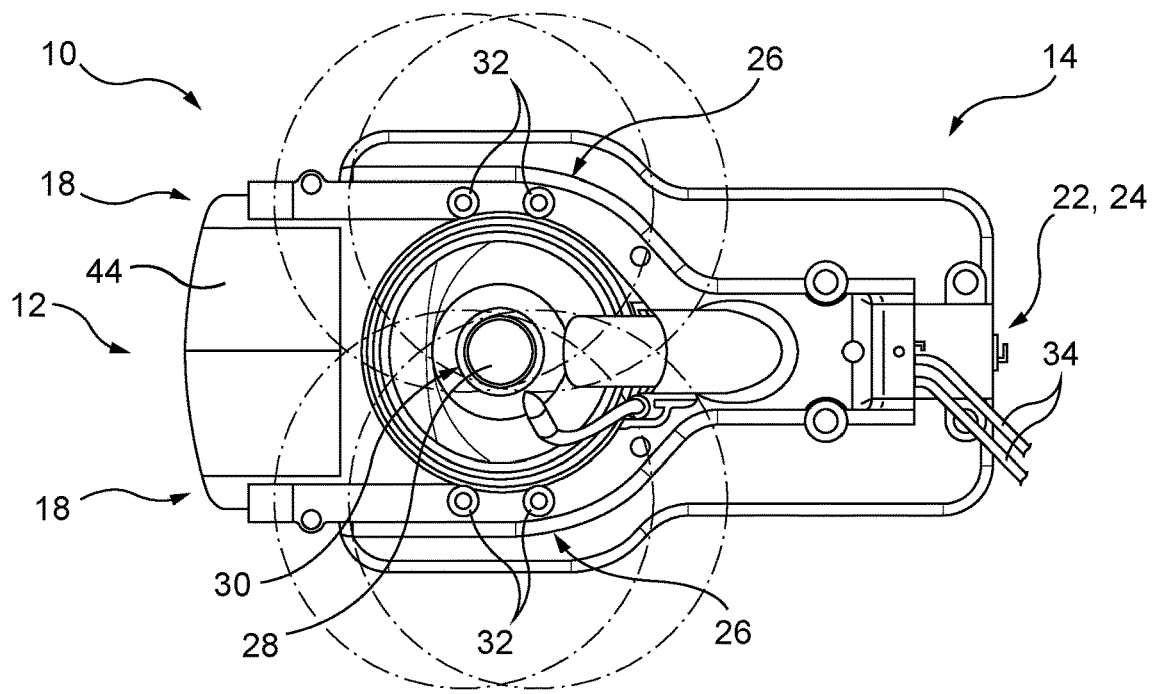
FIG. 2 is a schematic bottom view of the patient interface system.

FIG. 1 shows a schematic perspective view of a patient interface system 10 according to the invention according to a first embodiment. The patient interface system 10 serves for positioning a patient's eye (not shown) relative to a laser device (not shown) for the laser surgery and includes a patient interface 12 for coupling to the patient's eye and a patient interface holder 14 for arranging the patient interface 12 on the laser device. In the following, FIG. 1 will be explained in synopsis with FIG. 2, which shows a schematic bottom view of the patient interface system 10. Presently, the patient interface 12 is integrally formed of multiple assemblies adhered to each other, while the patient interface holder 14 is presently composed of three assemblies exemplary in number and orientation, which are screwed to each other and are explained in more detail in the following. The patient interface holder 14 includes a holding device 16, by means of which the patient interface 12, which can basically be a one-way or disposable part, can be reversibly coupled to the patient interface holder 14 and which is formed to position the patient interface 12 relative to the patient interface holder 14 in the coupled state. Hereto, the holding device 16 includes two opposing, groove-shaped guiding devices 18, along which a second positioning device 20 (see FIG. 4) of the patient interface 12 is forcibly guided movable for coupling and decoupling. Thereby, the patient interface 12 can be plugged into the holding device 16 of the patient interface holder 14 in drawer-like manner for coupling and again be withdrawn for decoupling.

One further recognizes that the patient interface holder 14 includes a connection device 22 for coupling a camera system 24 as well as an illumination device 26, by means of which at least a region of the patient's eye is illuminated perpendicular to a surface of a contact plate 28 of a first positioning device 30 of the patient interface 12. Hereto, the illumination device 26 presently includes four lighting means (e.g. LEDs) 32—exemplary in number and arrangement—the respective light cones of which are illustrated with circles in FIGS. 1 and 2. Since the patient interface 12 is composed of an optically transparent material in complete manner or at least in the region of the first positioning device 30, which is brought in abutment on the patient's eye for a laser-surgical treatment, the radiation of the lighting means 32 penetrates the wall of the patient interface 12 substantially funnel-shaped in this region and thereby indirectly irradiates both the surgical region below the contact plate 28, which can also referred to as contact glass, and directly the environment thereof.

Furthermore, the patient interface holder 14 and the patient interface 12 are connectable to a suction device (not shown), for example a vacuum pump, in a manner described in more detail in the following, to generate a relative negative pressure and to hold the patient interface 12 and its first positioning device 30, respectively, in abutment on the patient's eye. One in particular recognizes in FIG. 1 that all of the connection cables 34 for the camera system 24 and the illumination device 26 as well as a negative pressure hose 36 for connection of the suction device emerge from the patient interface holder 14 in the same direction and are arranged on a side of the patient interface holder 14 opposing the insertion side of the patient interface 12. Hereby, the patient interface 12 can be particularly simply and operationally reliably coupled to and uncoupled from the patient interface holder 14, respectively, wherein an engagement, positioning and connection to the camera system 24, the suction device and the illumination device 26 are effected at the same time with the coupling, without additional manual movements or working steps by a user being required hereto.

Figure 3:
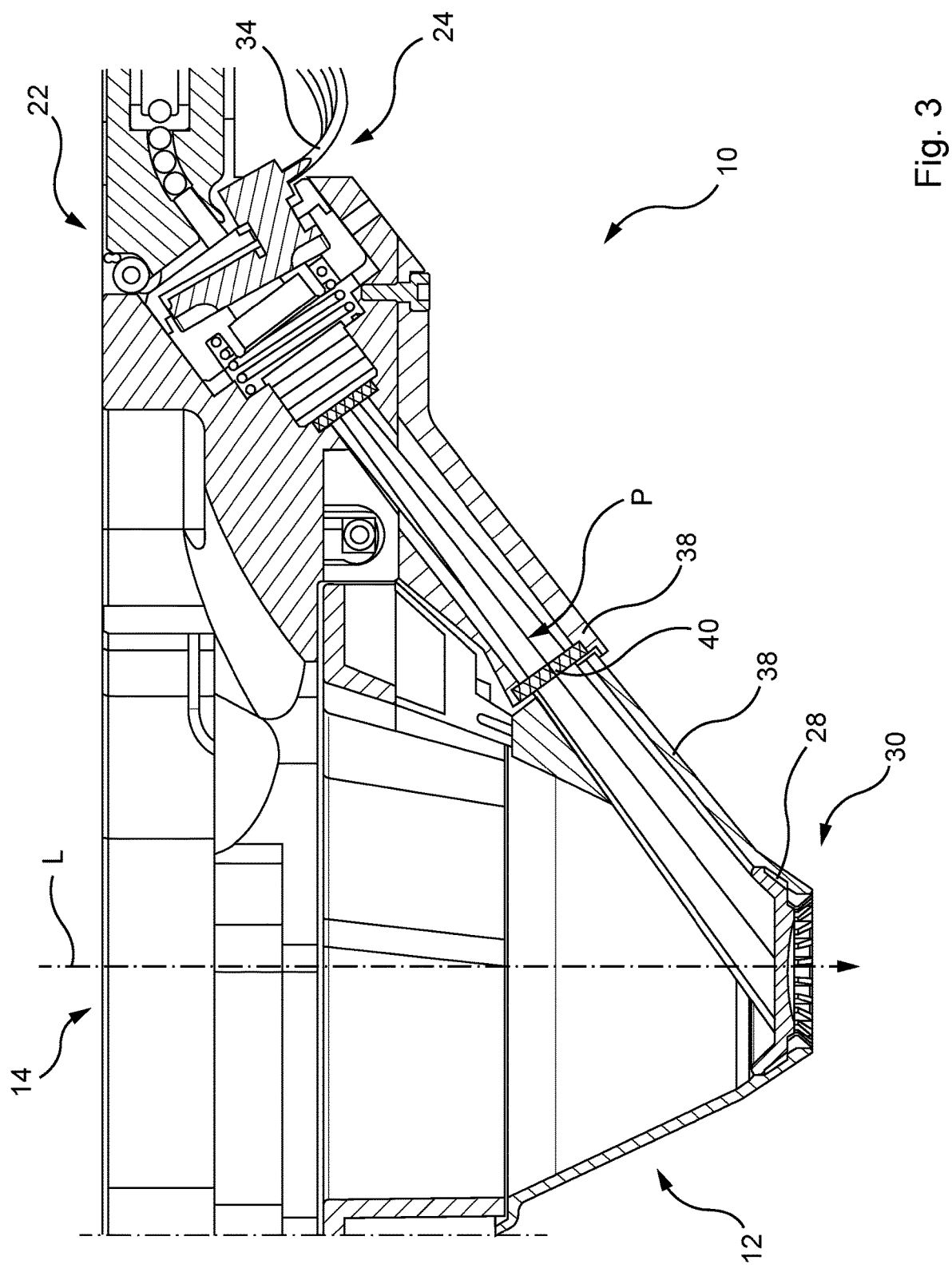
FIG. 3 is a schematic cross-sectional view of the patient interface system.

FIG. 3 shows a schematic cross-sectional view of the patient interface system 10. One in particular recognizes the camera system 24 coupled to the patient interface holder 14 by means of the connection device 22 and that the patient interface holder 14 and the patient interface 12 comprise channels 38 corresponding to each other, which commonly bound an optical path P between the connection device 22 and the first positioning device 30 in the coupled state of patient interface holder 14 and patient interface 12. Within the scope of the present disclosure, identical or functionally identical elements are usually denoted by identical reference characters if a varying denotation is not provided. The channel 38 of the patient interface holder 14 is closed by a window 40 transparent for wavelengths in the range visible to the human in an end region facing away from the connection device 22, such that foreign matter cannot enter and disturb the optical systems. The channels 38 and thereby the optical path P extend at an angle of about 45° to a direction of an intended laser radiation L of the laser device and to a surface of the contact plate 28 facing the laser device, respectively, in the coupled state of the patient interface 12 and the patient interface holder 14.

Figure 4:
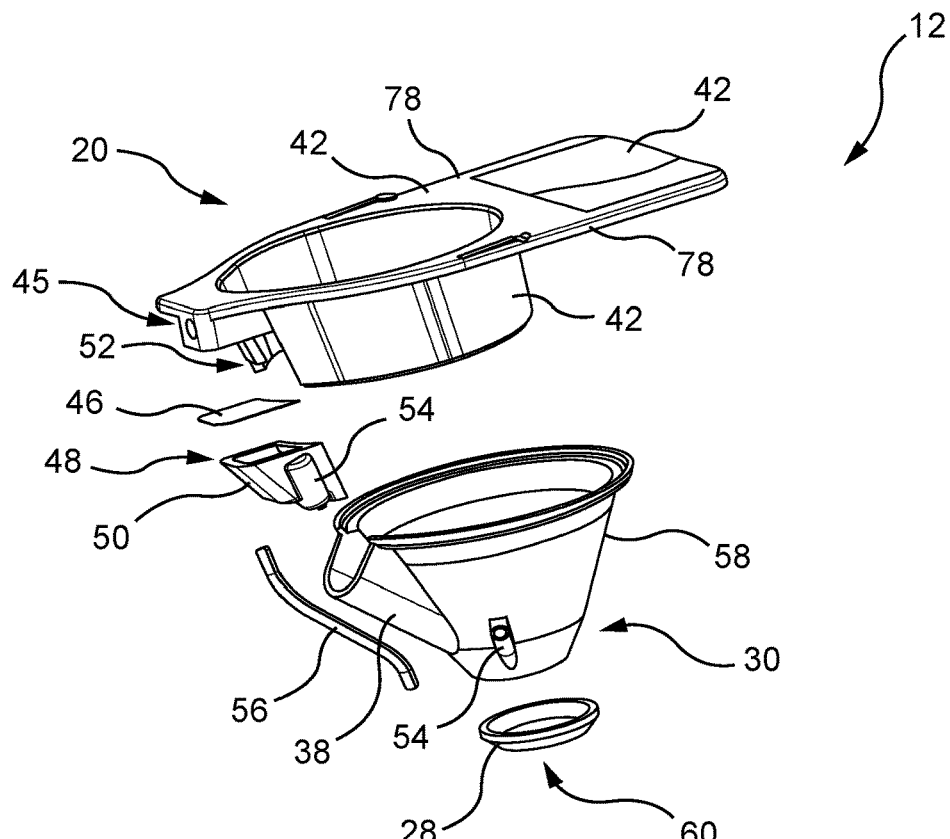
FIG. 4 is a schematic exploded representation of an embodiment of an inventive patient interface of the patient interface system.

FIG. 4 shows a schematic exploded representation of an embodiment of the patient interface 12 according to the invention. One sees that the patient interface 12 is composed of multiple assemblies, which are connected to each other by plug, shrinking and adhesive connections. From top to bottom, the assemblies include an interface body 42, which includes the second positioning device 20 as well as a holder 44, by means of which the patient interface 12 can be held by a user with thumb (from above) and index finger (from below), to couple the patient interface 12 to the patient interface holder 14 and to decouple it from the patient interface holder 14. The holder 44 has a concavely curved shape, which allows comfortable and safe gripping. One additionally recognizes a female fitting 45, with which a corresponding male connector 47 of the patient interface holder 14 engages in the coupled state with the patient interface holder 14 to also achieve a fluidic coupling besides the mechanical coupling. Furthermore, the patient interface 12 includes a filter element 46, which is arranged in a mounting opening 48 of an integrally formed collecting container 50. Since the mounting opening 48 is configured asymmetrical in the present example, the filter element 46 can only be inserted into the mounting opening 48 in the correct orientation, whereby a mounting without confusion is ensured. For example, this is reasonable if the filter element 46 requires a unidirectional flow direction. The collecting container 50 presently has a volume of about 120 mm$^3$, whereby it is large enough to securely avoid overflow or clogging during a laser-surgical intervention. The volume of about 120 mm$^3$ theoretically allows the performance of about five laser-surgical interventions, whereby a sufficient safety buffer is ensured. The collecting container 50 is in turn inserted into a corresponding mounting opening 52 of the interface body 42 together with the filter element 46 for mounting.

The collecting container 50 includes a fitting 54, in which a first end region of a negative pressure hose 56 is arranged. The opposing end region of the negative pressure hose 56 is inserted into a further fitting 54 for mounting, wherein the further fitting 54 is formed on a suction cup part 58 of the patient interface 12 and opens into a suction opening 64. The suction cup part 58 additionally includes the channel 38 for the camera system 24 and the first positioning device 30, which is fitted onto the patient's eye. Within the suction cup part 58, the contact plate 28 is fixed, for example adhered, in the region of the first positioning device 30.

The female fitting 45, the filter element 46, the collecting container 50 and the negative pressure hose 56 together form a fluid-conducting device 60, which together form a fluid path in the coupled state of patient interface 12 and patient interface holder 14, which fluidically couples a suction duct 62 of the patient interface holder 14 to a suction opening 64 of the patient interface in the region of the first positioning device 30 to be able to bring the first positioning device 30 in abutment on the patient's eye and to hold it on the patient's eye, respectively, by a relative negative pressure generated by means of the suction device. One recognizes that the fluid path is generally preferably arranged or formed outside of a path or passage channel extending through the patient interface 12, which forms an optical path P for a laser beam L of a laser device (see FIG. 10). Hereby, possible disturbances, which can occur if the fluid path and the optical path are formed in the same or a common channel, are reliably avoided.

Figure 5:
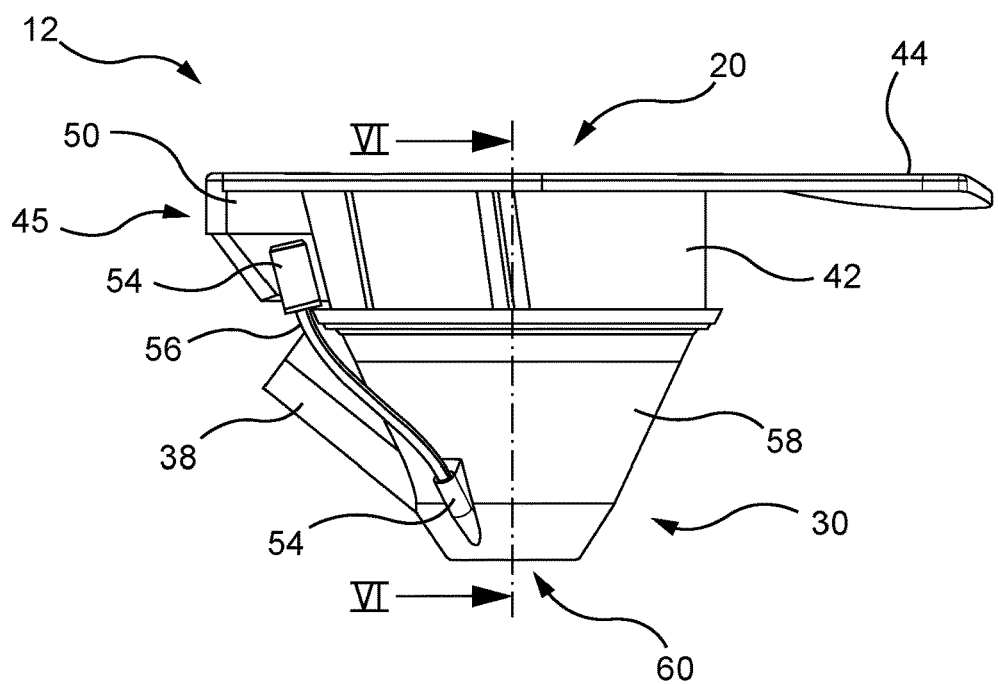
FIG. 5 is a schematic side view of the patient interface.

FIG. 5 shows a schematic side view of the patient interface 12 in the mounted state. One in particular recognizes the fluid-conducting device 60, which fluidically connects the first positioning device 30 to the female fitting 45 in the interface body 42 via the negative pressure hose 56, the collecting container 50 and the filter element 46.

Figure 6:
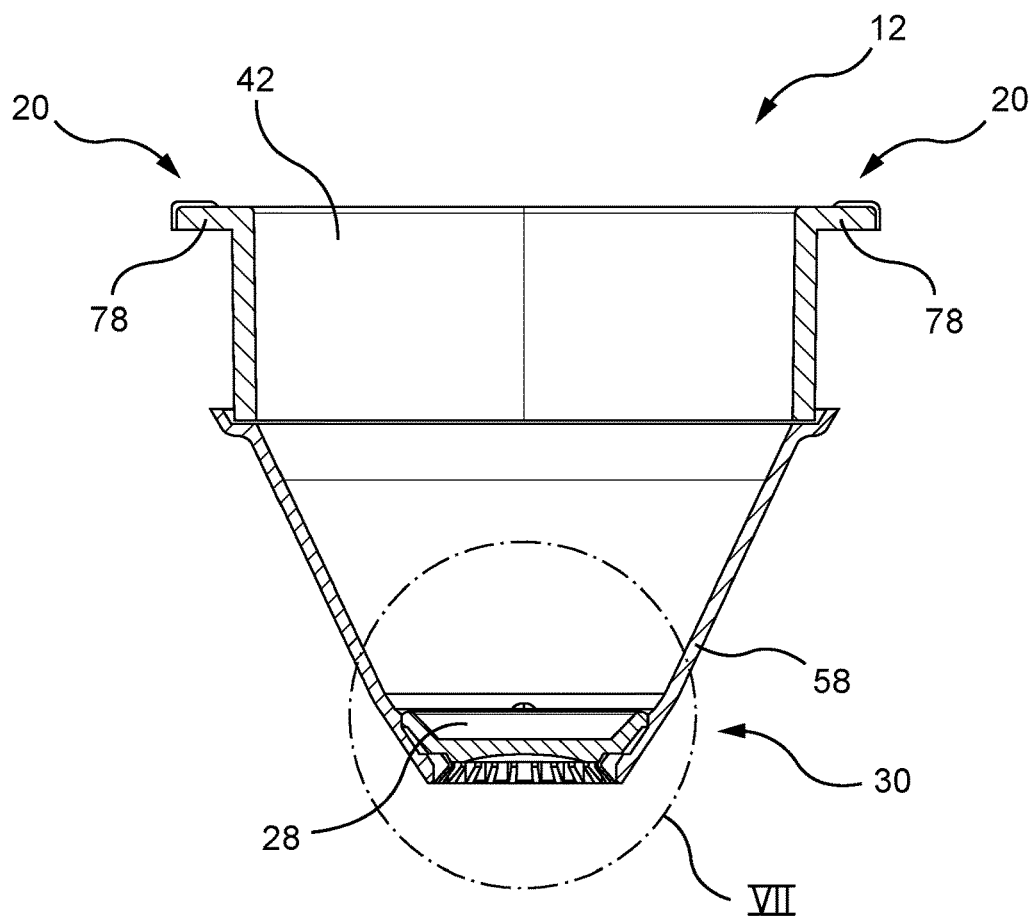
FIG. 6 is a schematic sectional view of the patient interface.
Figure 7:
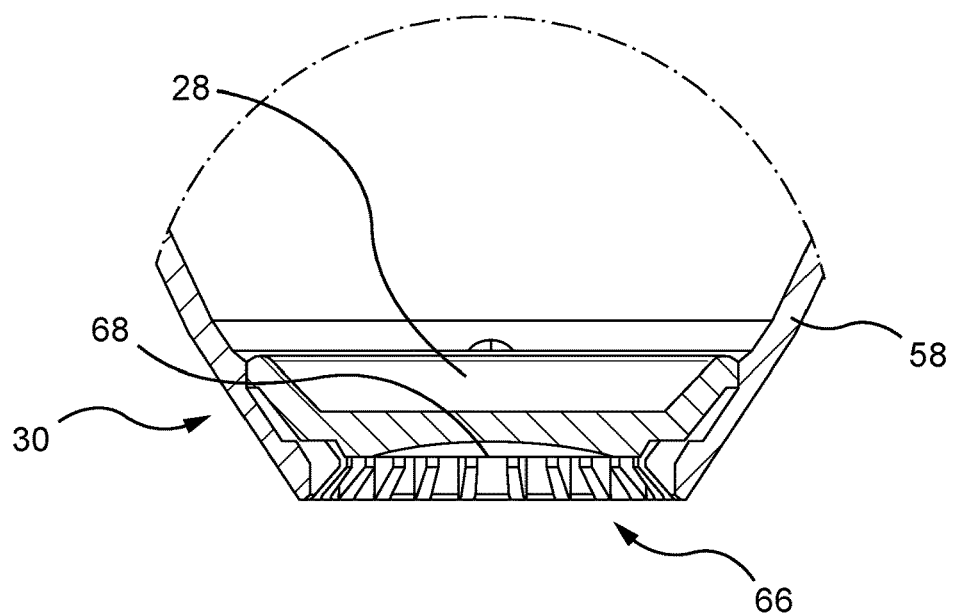
FIG. 7 is an enlarged view of the detail area VII shown in FIG. 6.

FIG. 6 shows a schematic sectional view of the patient interface 12 according to the sectional plane VI-VI shown in FIG. 5. In the following, FIG. 6 is explained in synopsis with FIG. 7, which shows an enlarged view of the detail area VII shown in FIG. 6. One recognizes the contact body 28 fluid-tightly adhered to the suction cup part 58, which has a concave bottom side, which bounds a cavity 66, into which the fluid-conducting device 60 opens. The first positioning device 30 further includes a plurality of teeth 68, which are annularly arranged spaced from each other in the end region of the patient interface 12 facing the patient's eye. The teeth 68 ensure an applanation of the patient's eye together with the contact body 28, wherein they minimize the applanation forces and suction load at the same time.

Figure 8:
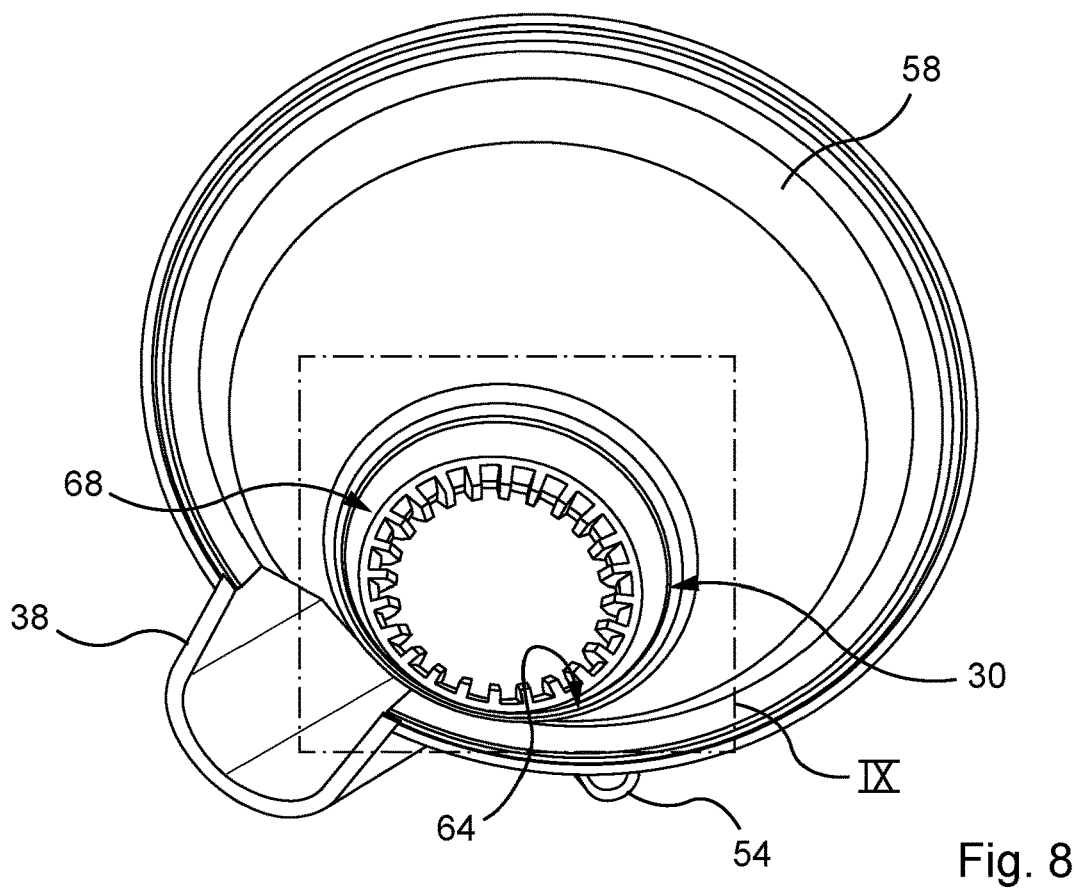
FIG. 8 is a schematic perspective view of a suction cup part of the patient interface from above.
Figure 9:
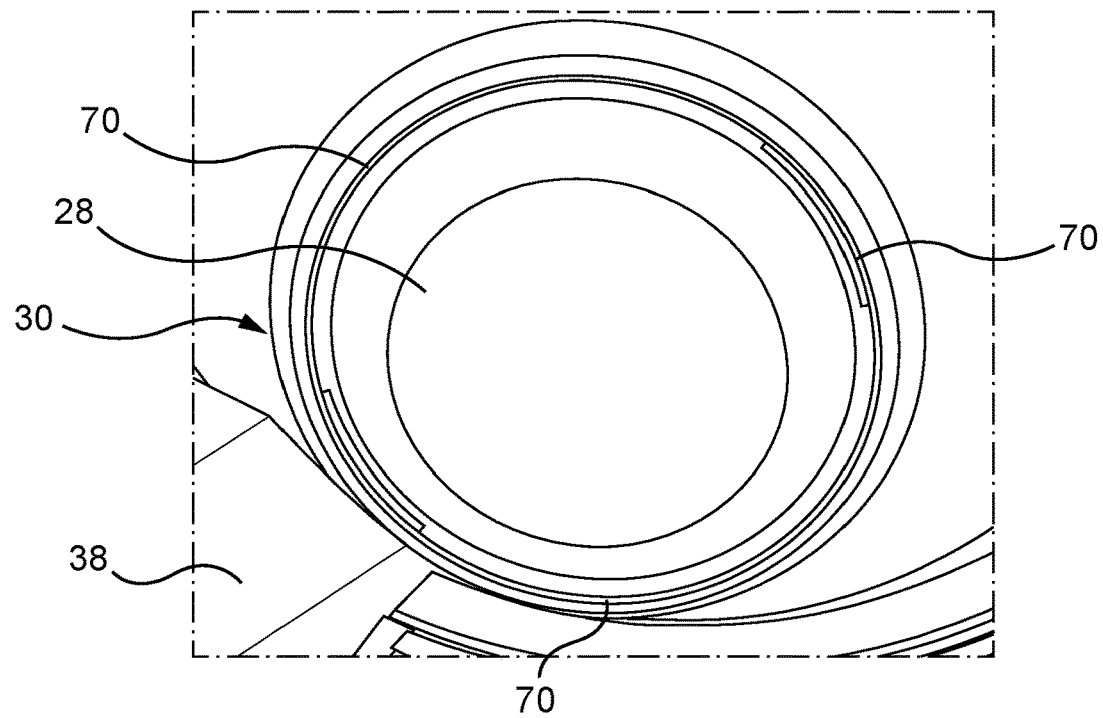
FIG. 9 is an enlarged view of the detail IX shown in FIG. 8.

FIG. 8 shows a schematic perspective view of the suction cup part 58 of the patient interface 12 from above, wherein the contact plate 28 is not yet mounted such that the annularly arranged teeth 68 of the first positioning device 30 as well as mounting ribs 70 for the contact plate 28 are recognizable. FIG. 9 shows an enlarged view of the detail IX shown in FIG. 8, wherein the contact plate 28 is now inserted into the suction cup part 58 in the region above the teeth 68 and adhered to it.

Figure 10:
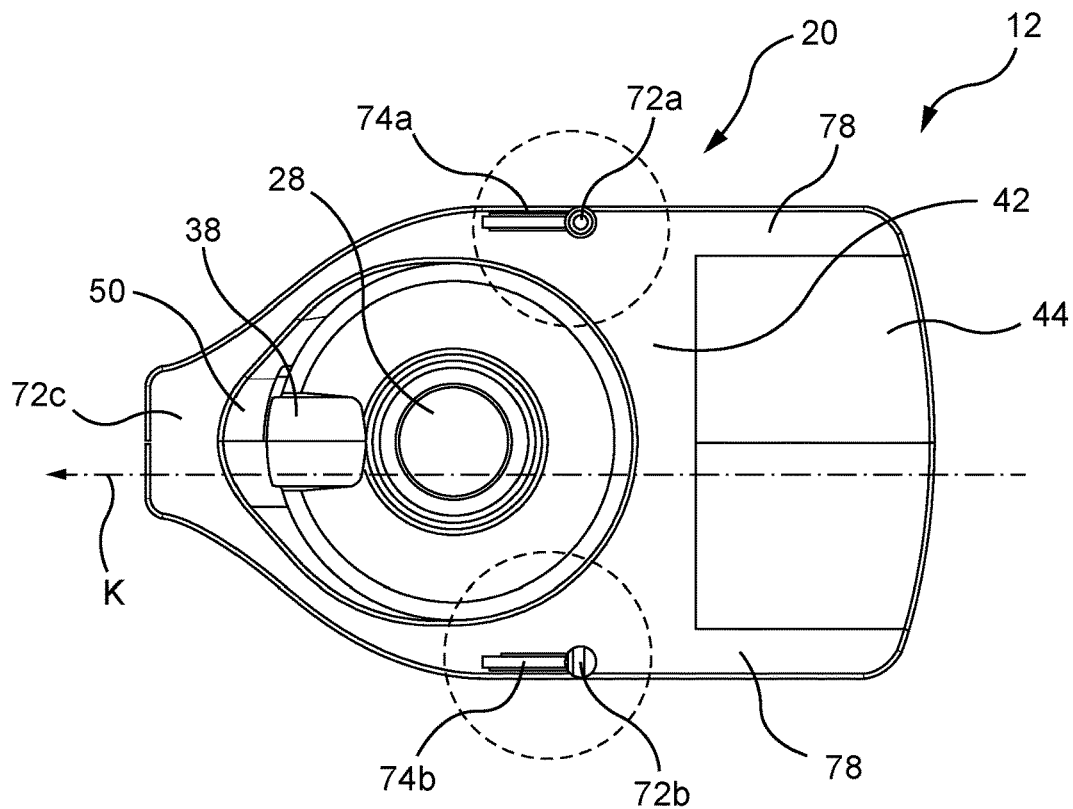
FIG. 10 is a schematic top view of the patient interface.

FIG. 10 shows a schematic top view of the patient interface 12. One in particular recognizes the second positioning device 20, which comprises three engaging surfaces 72a, 72b, 72c in the present embodiment, which are arranged in the shape of a triangle and between which a path or passage channel extending through the patient interface 12 for the laser beam L of the laser device is provided. Furthermore, the second positioning device 20 of the patient interface 12 includes two ramps 74a, 74b exemplary in number and arrangement, wherein the ramps 74a, 74b are arranged in front of their associated engaging surfaces 72a, 72b related to a coupling path K and ascend along the coupling path K. In the present embodiment, the engaging surface 72a has a frustoconical geometry, while the engaging surface 72b is slit-shaped and the engaging surface 72c is flat. In the coupled state of patient interface 12 and patient interface holder 14, the engaging surfaces 72a-c cooperate with corresponding spring-loaded engaging bodies 76a-c of the patient interface holder 14, whereby the following restrictions of the three translational and three rotational degrees of freedom result in the following embodiment:

Engaging surface 72a: 2 translational degrees of freedom blocked engaging surface 72b: 2 rotational degrees of freedom blocked engaging surface 72c: 1 rotational degree of freedom blocked This means that the patient interface 12 is not rigidly coupled to the patient interface holder 14 in the coupled state, but slightly movable only in z-direction, that is perpendicular to the applanated patient's eye and translational along the direction of the laser beam L, respectively, to be able to compensate for tolerances and to allow a simpler coupling and decoupling without having to accept losses with respect to the correct positioning. Furthermore, collars 78 of the second positioning device 20 are apparent, which are shifted into the groove shaped guiding devices 18 in coupling and forcibly guided moved along the substantially linear coupling path K in the manner of a drawer. Due to the ramps 74a, 74b, a continuously increasing insertion force is required for coupling until the engaging bodes 76a, 76b engage with the engaging surfaces 72a, 72b. This generates a unique haptic feedback for a user about the progress of the coupling operation as well as about the effected coupling due to the engagement of the engaging bodes 76a, 76b.

Figure 11:
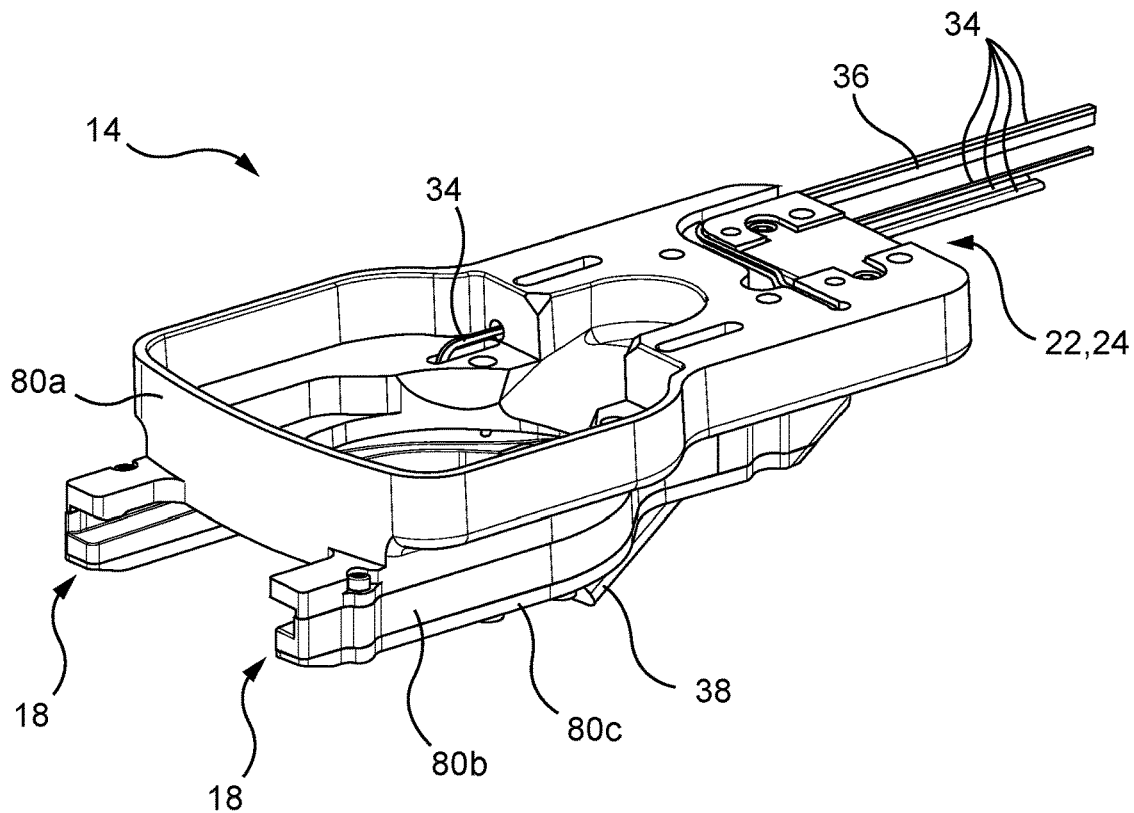
FIG. 11 is a schematic perspective view of an embodiment of an inventive patient interface holder of the patient interface system.

FIG. 11 shows a schematic perspective view of the embodiment already shown in FIG. 1 of the inventive patient interface holder 14 of the patient interface system 10 without coupled patient interface 12. One in particular recognizes that the patient interface holder 14 presently includes three assemblies 80a-c connected to each other. Therein, the assembly 80a functions as an upper holding group, the assembly 80b functions as a lower holding group and the assembly 80c functions as an illumination holder. The assemblies 80a, 80b together form the groove-shaped guiding device 18. Moreover, the assembly 80a includes the connection device 22, into which the camera system 24 is inserted.

Figure 12:
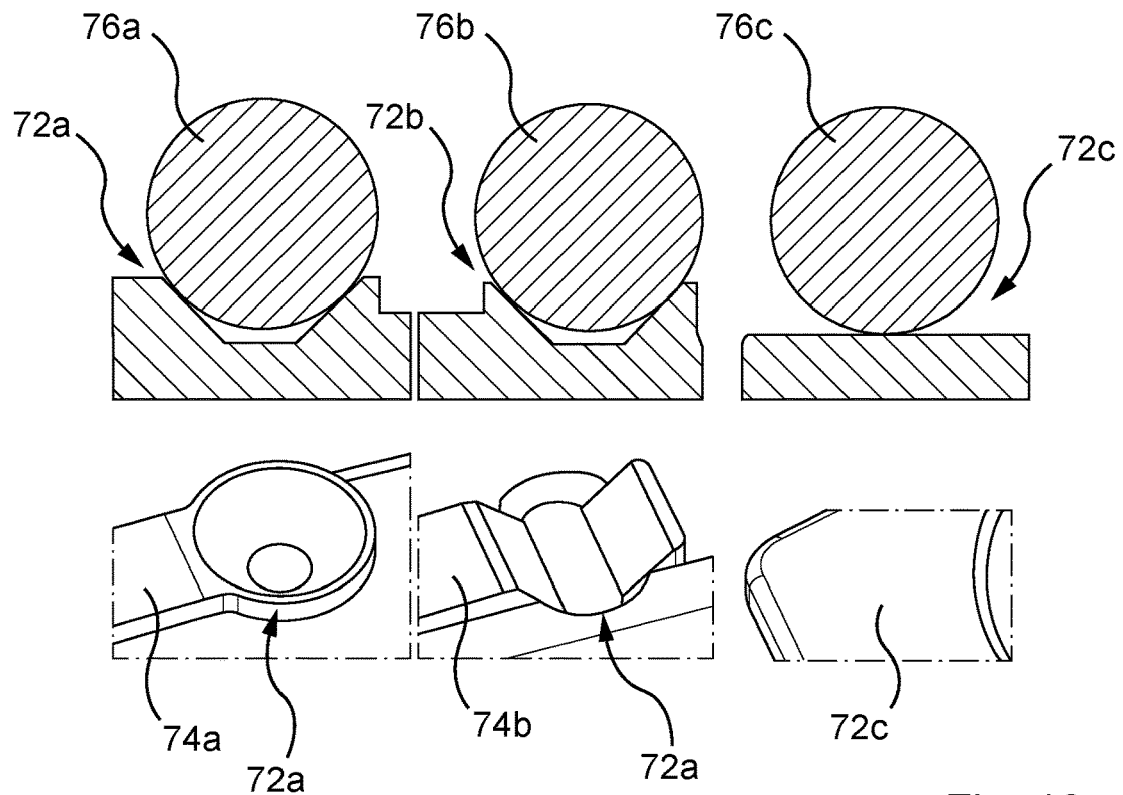
FIG. 12 is a schematic lateral sections of engaging bodies of the patient interface holder and perspective top views to their corresponding engaging surfaces of the patient interface.

FIG. 12 shows schematic lateral sections of engaging bodies 76a-c of the patient interface holder 14, which cooperate with their corresponding engaging surfaces 72a-c of the patient interface 12 in the coupled state of patient interface 12 and patient interface holder 14. The engaging bodes 76a-c are presently ceramic balls of identical diameter, which are rigidly fixed to the patient interface holder 14. These ceramic balls are mechanically very resistant on the one hand and can easily slide along the surface and the ramps 74a, 74b of the second positioning device 20 during the coupling operation on the other hand. It is understood that varying materials such as for example steel or plastic can basically also be used. The individual engaging bodies 76a-c can basically also be composed of different materials and/or have varying geometries. Below the individual pairings, perspective partial top views of the engaging surfaces 72a-c of the patient interface 12 without the engaging bodies 76a-c are respectively shown.

Figure 13:
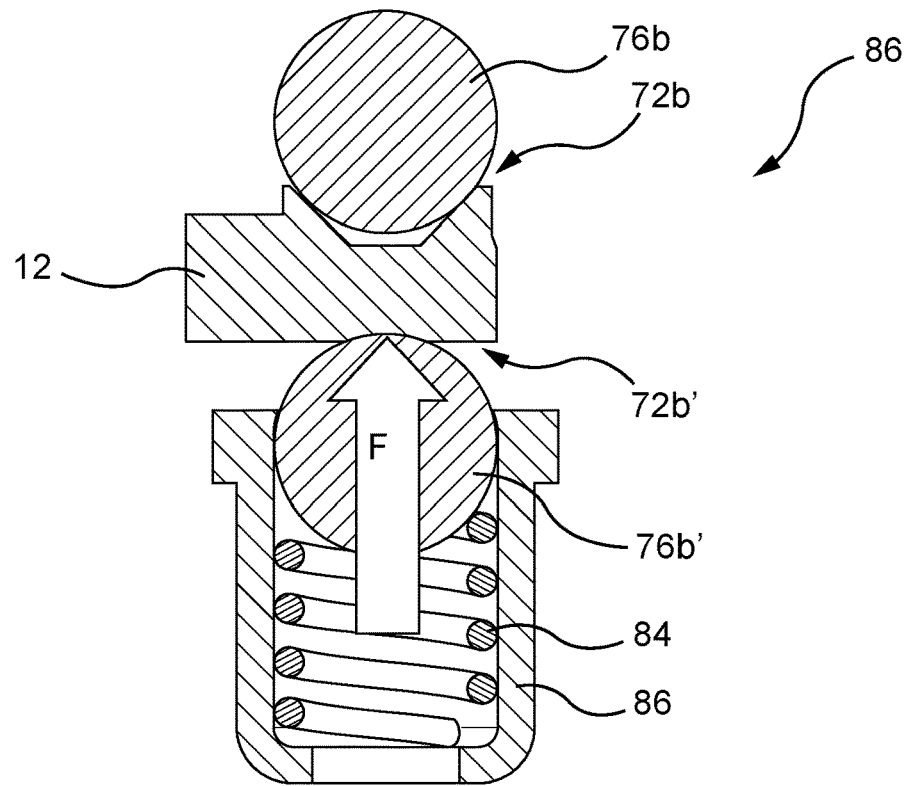
FIG. 13 is a partial lateral sectional view of the patient interface in the region of engaging surfaces opposing each other, which cooperate with corresponding engaging bodies of the patient interface holder.

FIG. 13 shows a partial lateral sectional view of the patient interface 12 in the region of engaging surfaces 72b, 72b' opposing each other, which cooperate with corresponding engaging bodes 76b, 76b' of the patient interface holder. In contrast to the engaging body 76b, the engaging body 76b' is spring-loaded and ensures a reliable coupling of patient interface 12 and patient interface holder 14 since the patient interface 12 and patient interface holder 14 are only movable relative to each other with overcoming an overall spring force of all of the spring-loaded engaging bodies 76a'-c' in the coupled state. With overcoming the overall spring force, however, at least a translational movement in z-direction, that is against the spring forces F, is possible such that the patient interface 12 and patient interface holder 14 are not rigidly, but resiliently connected and do not behave like an integral body, respectively, also in the coupled state. The engaging bodies 76b, 76b' as well as the engaging bodies 76a, 76a', 76c, 76c' not explicitly illustrated form an engaging device 82 together with their corresponding engaging surfaces 72a-c, 72a'-c'. The engaging bodies 76a'-c' too are presently formed as ceramic balls and arranged in a housing 86 together with respective springs 84. It is understood that the engaging bodies 76a'-c' can also be formed of varying materials and/or have varying geometries. Similarly, it can be provided that all of the springs 84 have identical or different spring forces F.

Figure 14:
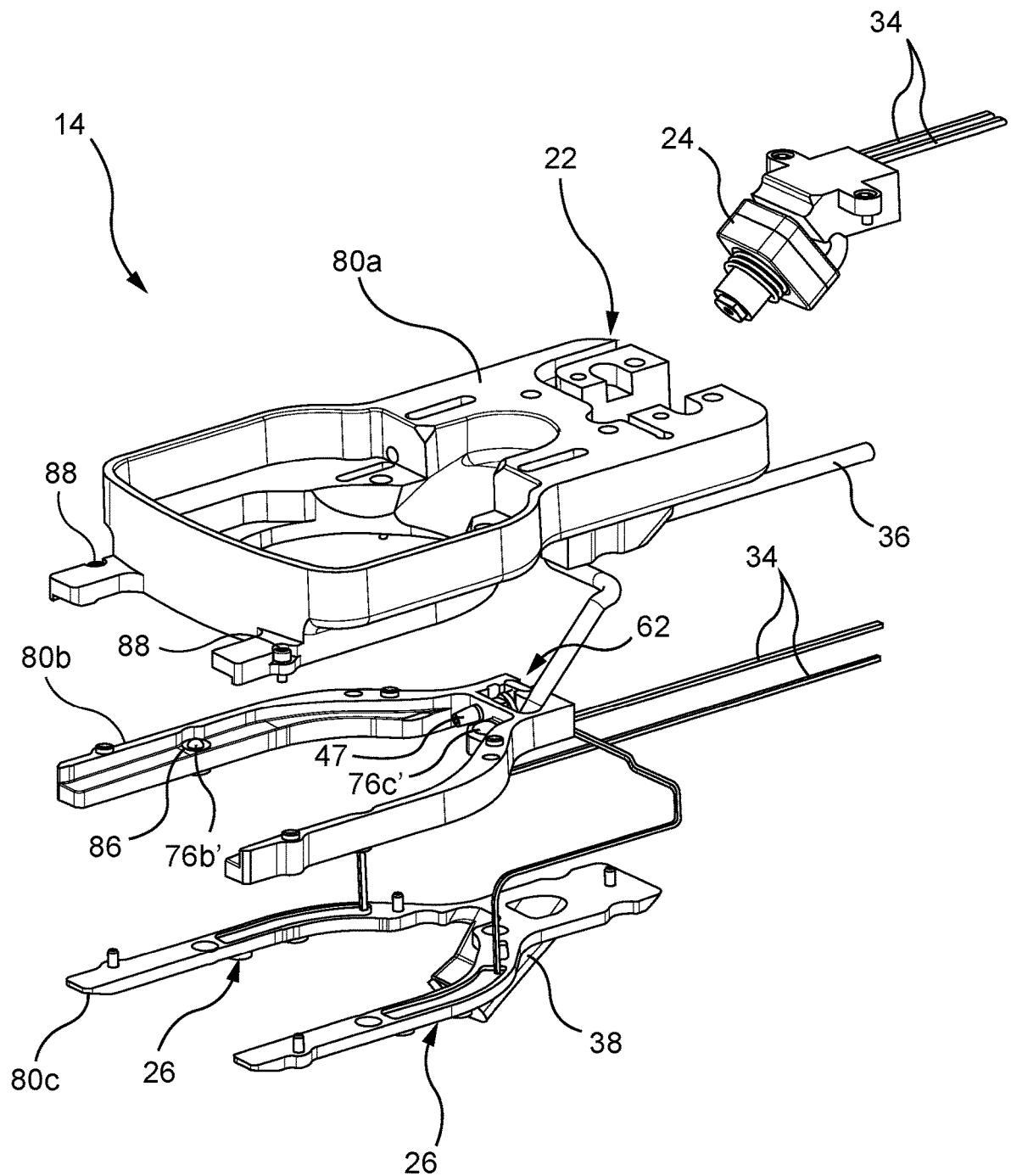
FIG. 14 is a schematic exploded representation of the patient interface holder.

FIG. 14 shows a schematic exploded representation of the patient interface holder 14. One recognizes that the camera system 24 is pluggable into the connection device 22 and capable of being screwed to the first assembly 80a in the shown embodiment. The assembly 80b supports the spring-loaded engaging bodies 76a'-c' supported in their housings 86. Furthermore, one recognizes the suction duct 62 with the male connector 47, which is connected to the negative pressure hose 36. The illumination device 26 presently including four LEDs, which is integrated in the third assembly 80c and is electrically supplied via its connection cables 34, is also well recognizable.

Figure 15:
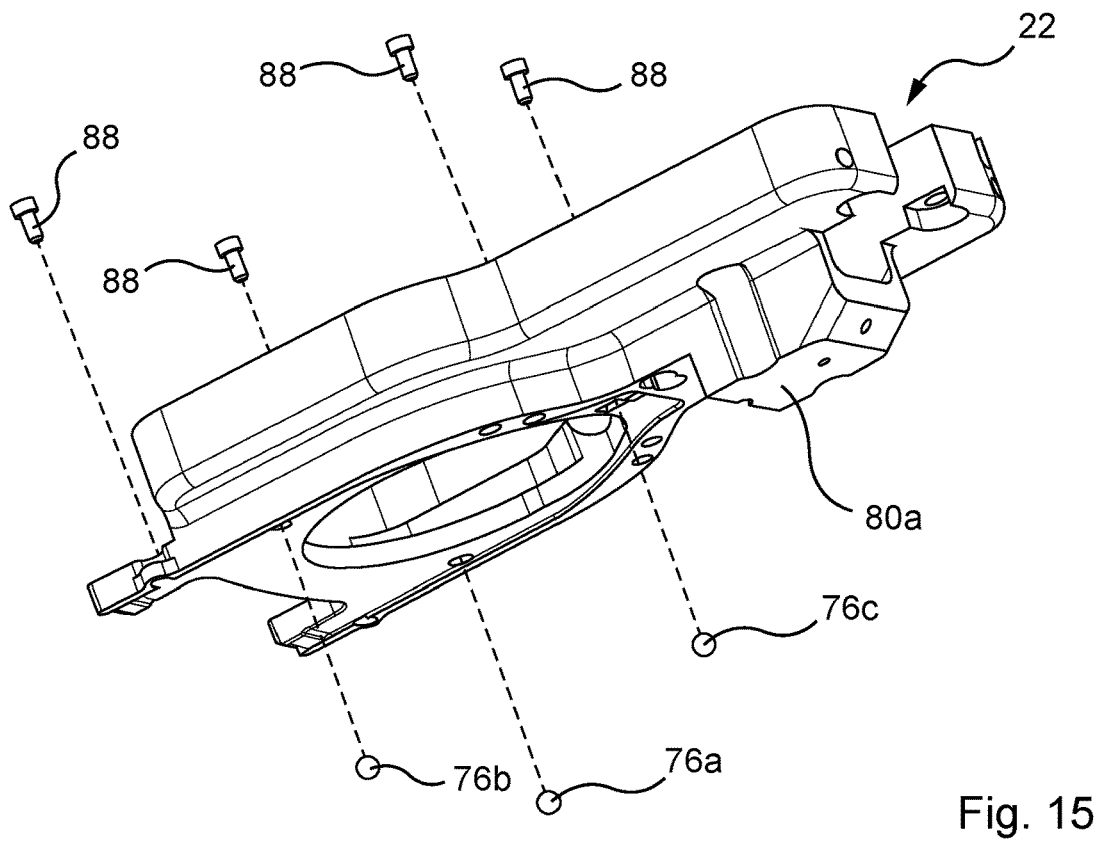
FIG. 15 is a schematic exploded representation of a first assembly of the patient interface holder.

FIG. 15 shows a schematic exploded representation of the first assembly 80a of the patient interface holder 14 from obliquely below. Here, the engaging bodies 76a-c not spring-loaded, but rigidly supported in the first assembly 80a are in particular apparent, which are inserted into corresponding mounting openings in the assembly 80a. Furthermore, four screws 88 are illustrated as fixing means, by means of which the assemblies 80a-c are screwed to each other. It is understood that other fixing means, a varying number of fixing means as well as a varying orientation of the fixing means can also be provided.

Figure 16:
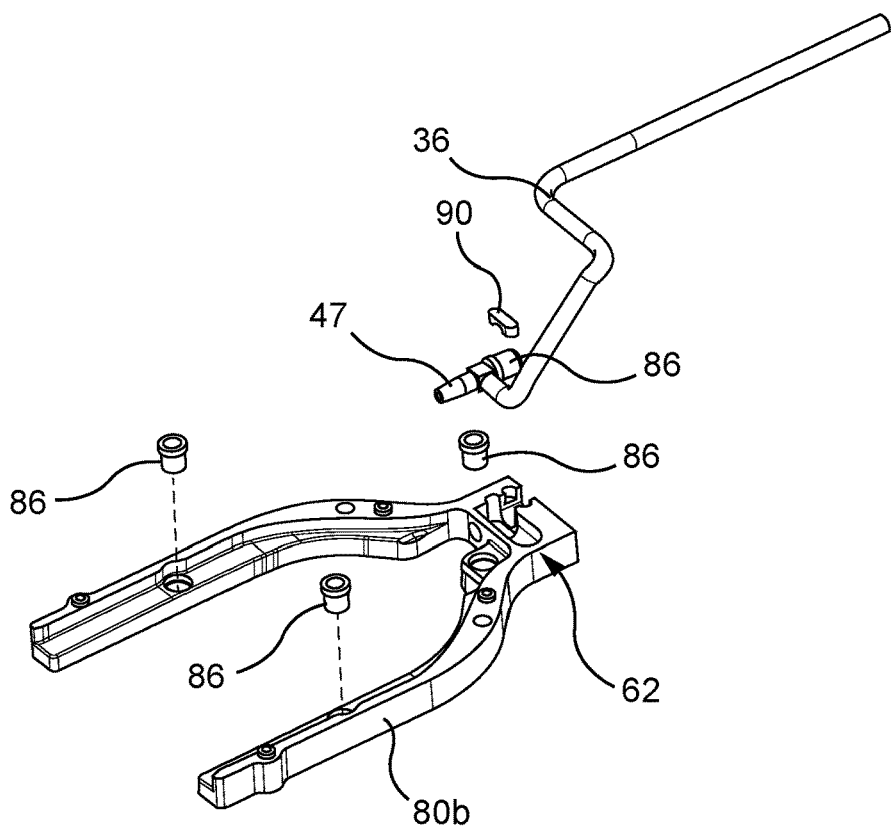
FIG. 16 is a schematic exploded representation of a second assembly of the patient interface holder.

FIG. 16 shows a schematic exploded representation of the second assembly 80b of the patient interface holder 14. Therein, only the housings 86 of the spring-loaded engaging bodies 76a'-c' are shown of the engaging device 82, which are inserted into corresponding mounting openings of the second assembly 80b. Furthermore, it is apparent that the negative pressure hose 36 is connected to the male connector 47 and inserted into the suction duct 62. The connector 47 is in turn applied with force by a further spring-loaded engaging body 76d', wherein also only the housing 86 of it is shown. The housing 86 of this engaging body 76d' is fixed to the second assembly 80b by means of a bracket 90.

Figure 17:
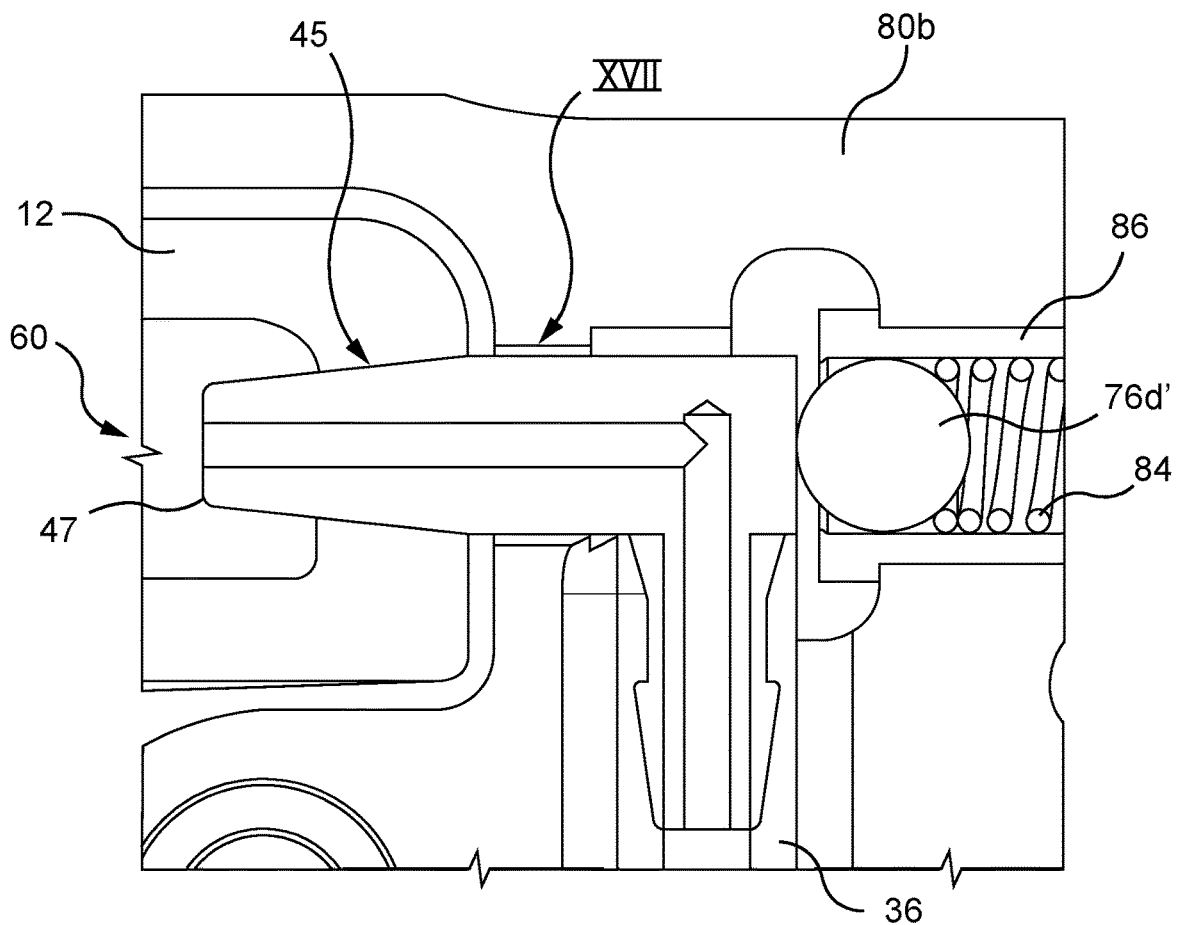
FIG. 17 is a schematic and partial sectional view from above to a suction duct of the patient interface holder and a part of a fluid-conducting device of the patient interface.

FIG. 17 shows a schematic and partial sectional view from above to the suction duct 62 of the patient interface holder 14 as well as a part of the fluid-conducting device 60 of the patient interface 12 coupled to the patient interface holder 14. Due to the engagement of the male connector 47 with the female fitting 45, the patient interface holder 14 and the patient interface 12 are fluidically coupled such that the patient interface 12 can be held in abutment on the patient's eye by means of a relative negative pressure, which is generated by a suction device connected to the negative pressure hose 36. Therein, the female fitting 45 comprises an inner cone, in which a corresponding outer cone of the male connector 47 is arranged in the coupled state. The outer cone and the inner cone presently have a contact angle of about 12° according to amount, wherein a gas-tight connection is ensured on the one hand and a fast and uncomplicated coupling and decoupling with a force of at most about 2 N by an axial movement along the coupling path K are ensured on the other hand. Although the male connector 47 and the female fitting 45 can also be interchanged, the shown arrangement of the female fitting 45 at the patient interface 12 has the advantage that the risk of contaminations between unpacking and coupling the patient interface 12 is reduced since the contact surface of the female fitting 45 is less severely exposed to the environment than with a male connector 47. By reducing the risk of contamination, later connecting problems are also avoided besides possible hygienic problems. While the male connector 47 is in direct contact with the wall of the female fitting 45, a certain backlash is allowed in the region denoted by the arrow XVII.

Figure 18:
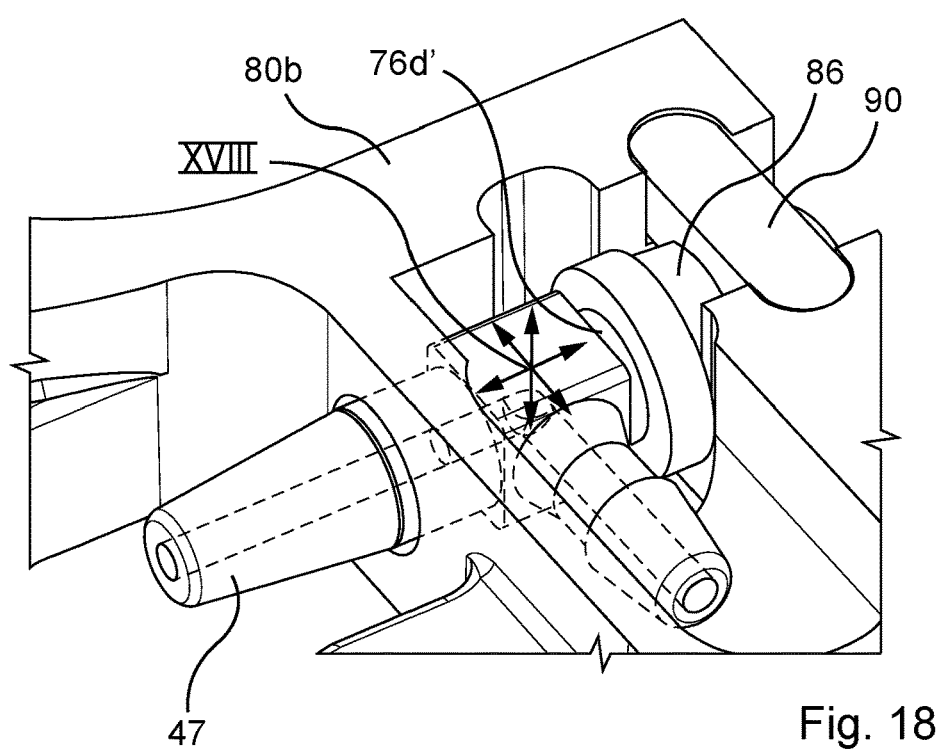
FIG. 18 is a schematic and partially transparent perspective view of the region of the patient interface system shown in FIG. 17.
Figure 19:
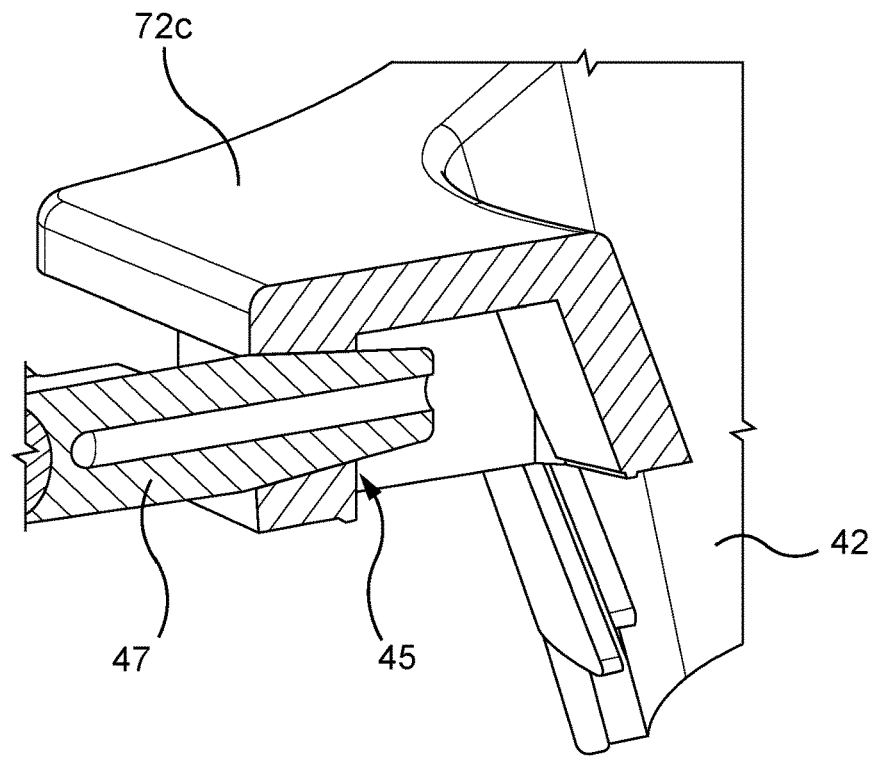
FIG. 19 is a schematic sectional view of a male connector, which engages with a corresponding female fitting of the patient interface.

As one sees in FIG. 18, which shows a schematic and partially transparent perspective view of the region of the patient interface system 10 shown in FIG. 17, the male connector 47 is floating supported and movable in all three spatial directions, wherein the connector 47 is pressed towards the female fitting 45 by the engaging body 76d'. This allows a particularly reliable and gas-tight connection with compensation for possible manufacturing tolerances. For further clarification, FIG. 19 shows a schematic sectional view of the connector 47, which engages with the female fitting 45 of the patient interface 12.

Figure 20:
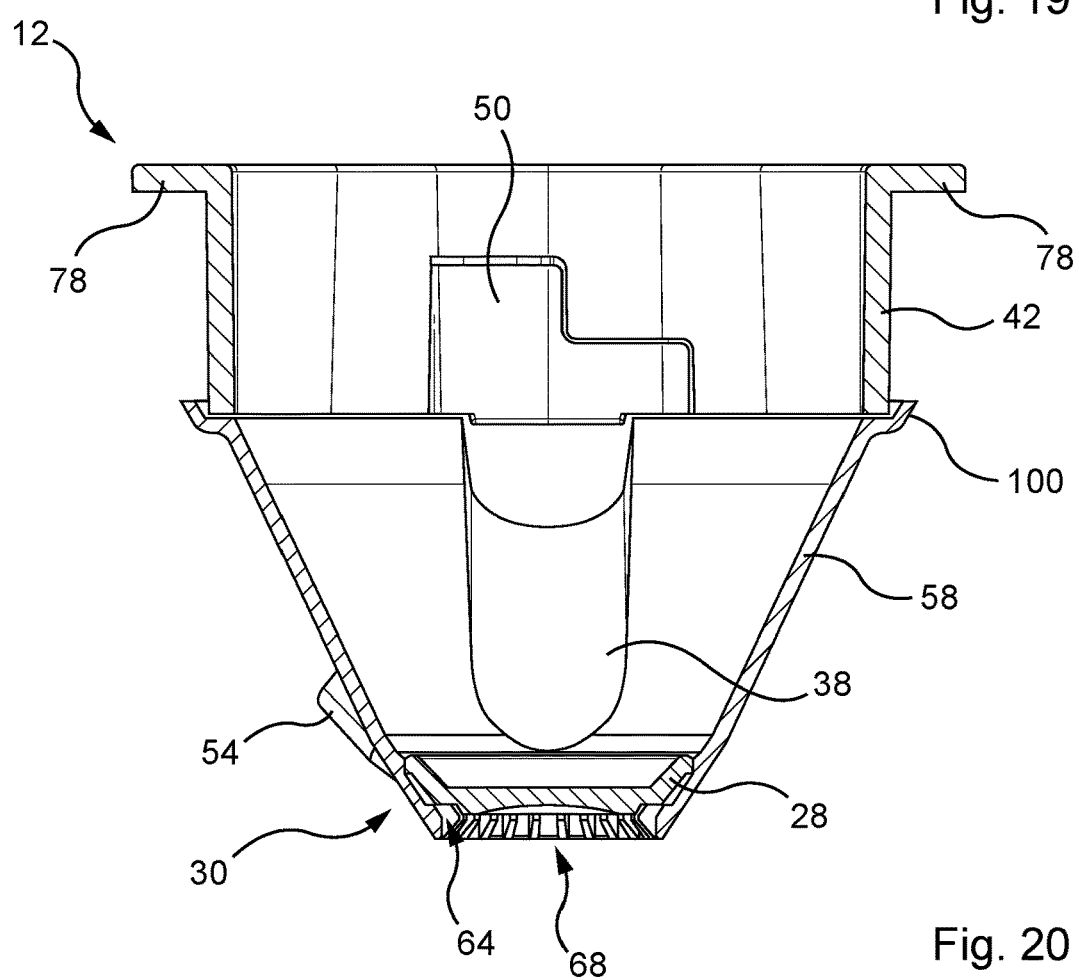
FIG. 20 is a schematic sectional view of an embodiment of the patient interface.

FIG. 20 shows a schematic sectional view of an embodiment of the patient interface 12. One in particular recognizes the suction opening 64, into which the fitting 54 opens. Furthermore, it becomes clear that the suction cup part 58 comprises a circumferential collar 100, into which the interface body 42 is inserted and adhered to the suction cup part 58. By the configuration of the collar 100, self-centering is effected upon mounting. In that the collar 100 also comprises a vertical section besides a horizontal section, on which the interface body 42 rests, horizontal and vertical tolerances can be compensated for by the geometric configuration of the collar 100. Therein, the collar 100 forms a reservoir for excessive adhesive and ensures that the adhesive is drawn into the gap between interface body 42 and suction cup part 58 by capillary forces. This ensures a high-quality firmly bounded connection of both assemblies of the patient interface 12.

Figure 21:
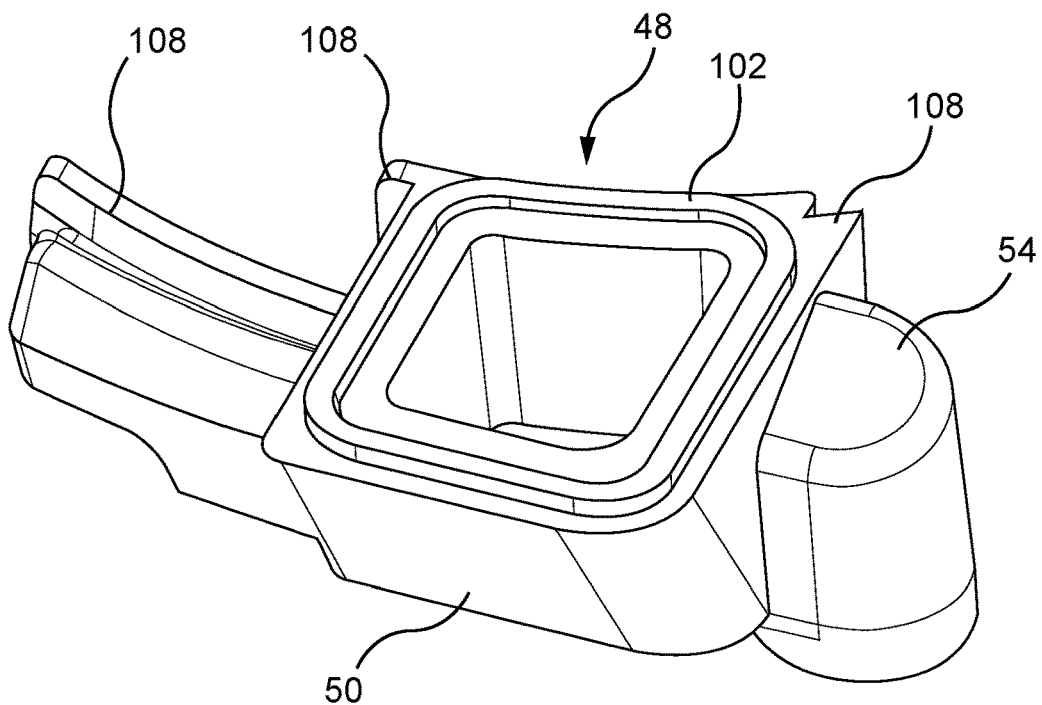
FIG. 21 is a schematic perspective view of an embodiment of a collecting container.
Figure 22:
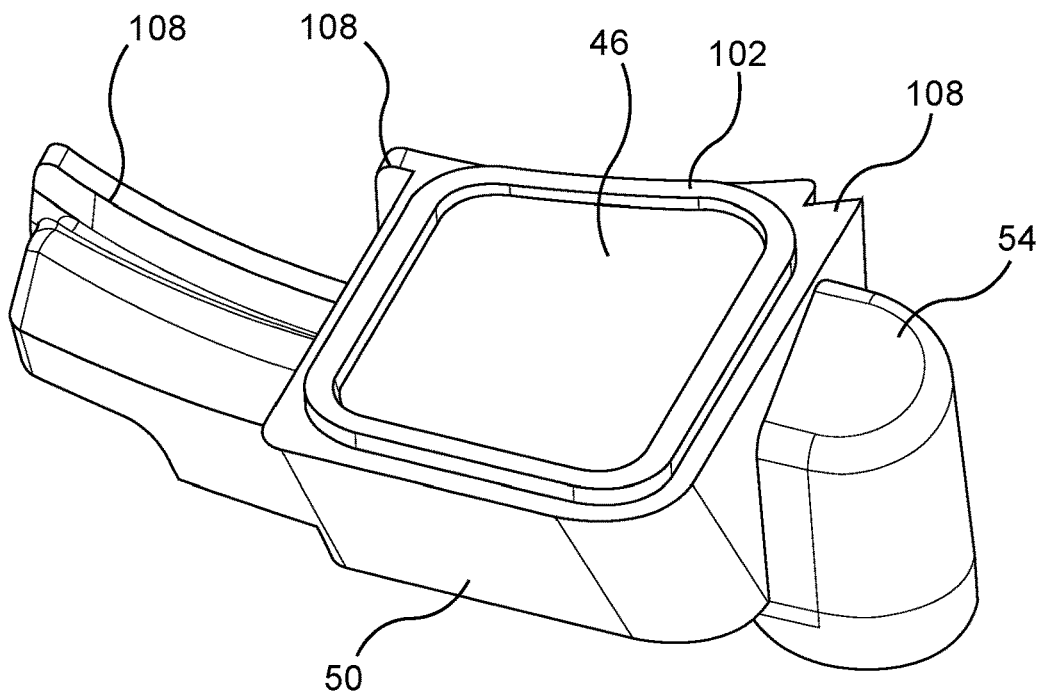
FIG. 22 is a schematic perspective view of the collecting container, which is provided with a filter element.

FIG. 21 shows a schematic perspective view of an embodiment of a collecting container 50 and is explained in synopsis with FIG. 22 in the following, which shows a schematic perspective view of the collecting container 50, which is provided with the filter element 46. One sees in FIG. 21 that the mounting opening 48 for the filter element 46 is asymmetrically formed and comprises a circumferential edge 102. When the collecting container 50 with the filter element 46 is inserted into its associated mounting opening 52 of the interface body 42 and heated, this edge 102 collapses, whereby the gap between collecting container 50 and interface body 42 decreases and the filter element 46 is operationally reliably and fluid-tightly clamped between both parts.

Figure 23:
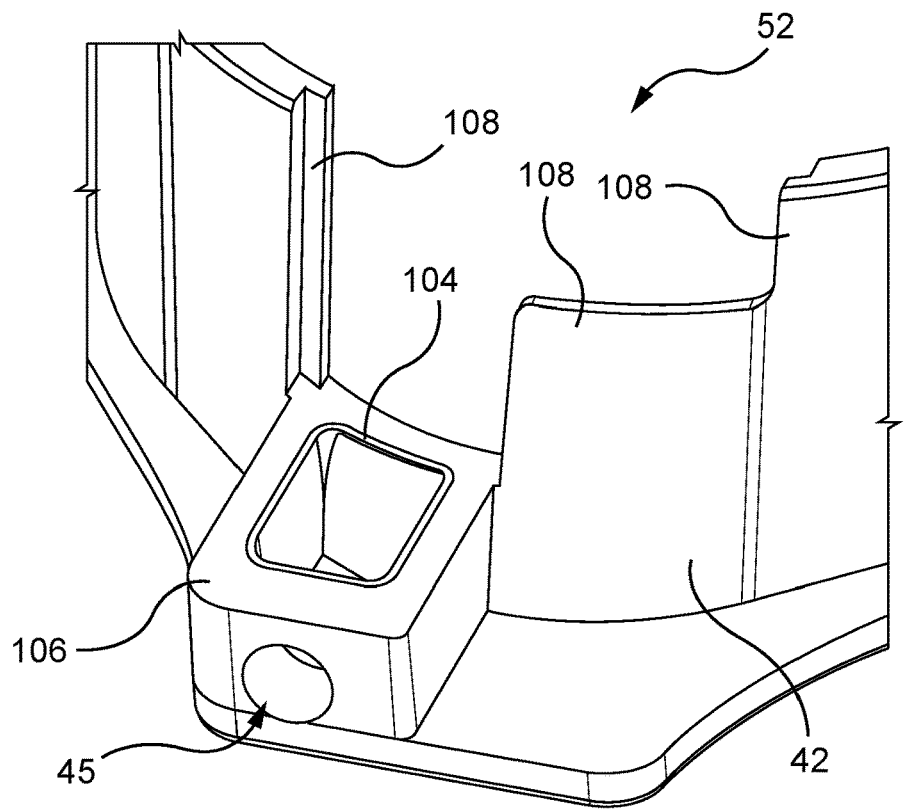
FIG. 23 is a schematic perspective view of the patient interface in the region of a mounting opening for the collecting container.
Figure 24:
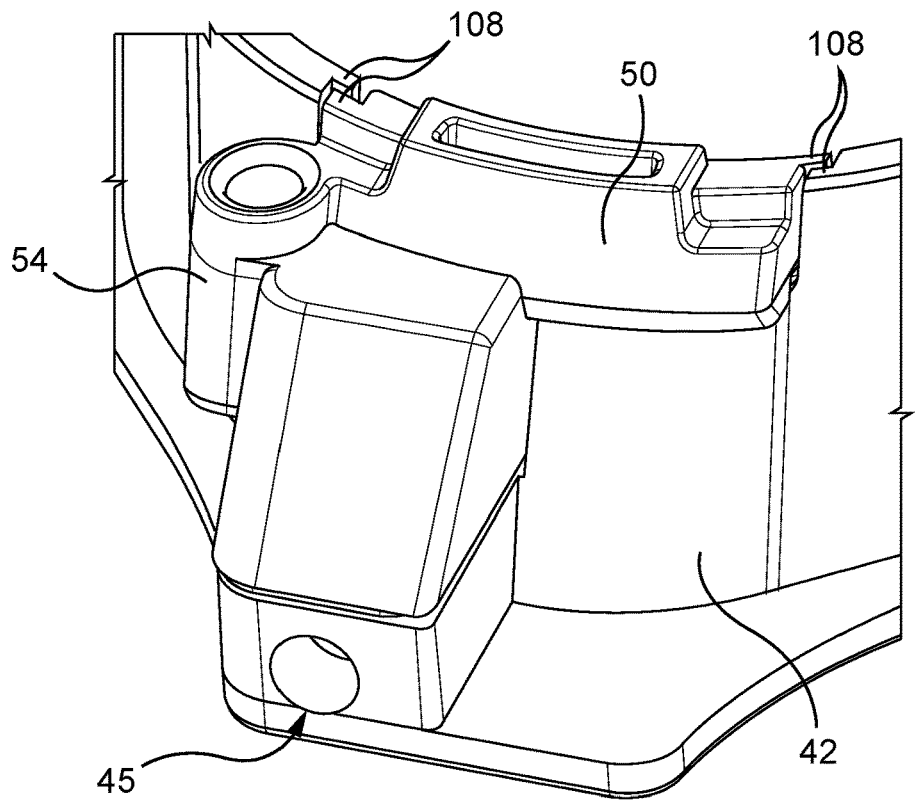
FIG. 24 is a schematic perspective view of the patient interface, wherein the collecting container is arranged in the mounting opening.

FIG. 23 shows a schematic perspective view of the patient interface 12 in the region of its mounting opening 52 for the collecting container 50. The walls of the interface body 42 bounding the mounting opening 52 comprise ribs 108 directed outwards on the one hand and inwards on the other hand, such that the collecting container 50, which comprises complementary ribs 108, can be shifted into the mounting opening 52 without tilt. A support surface 106 of the patient interface 12 comprises a circumferential lip 104 on its inner circumference, which contributes to laterally sealing the filter element 46 together with the edge 102 in the mounted state. Therefore, fluid can only flow from the fitting 54 through the collecting container 50, the filter element 46 and the fitting 54. FIG. 24 shows a schematic perspective view of the patient interface 12, wherein the collecting container 50 is arranged and fixed in the mounting opening 52.

Figure 25:
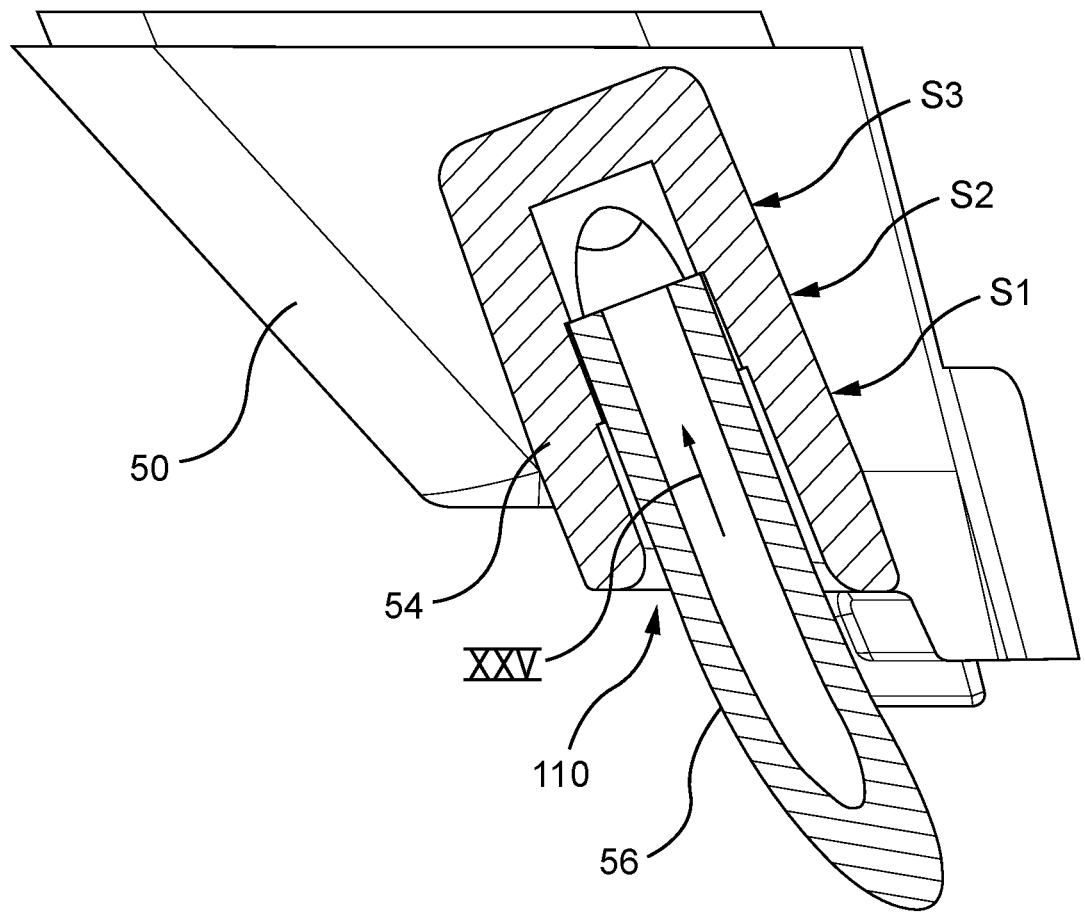
FIG. 25 is a schematic sectional view of the collecting container in the region of a fitting, in which an end region of a negative pressure hose is arranged.

FIG. 25 shows a schematic sectional view of the collecting container 50 in the region of its fitting 54. The fitting 54 comprises a mounting duct 110, in which an end region of the negative pressure hose 56 is arranged. The mounting duct 110 in turn has an inner diameter decreasing in three steps along a mounting direction XXV starting from an introduction opening, the inner diameter of which is larger than an outer diameter of the negative pressure hose 56. In the first section S1, which serves for fixing, the inner diameter of the mounting duct 110 is larger than the outer diameter of the negative pressure hose 56 as mentioned and wetted with an adhesive for mounting. In the second section S2, which serves for positioning, the inner diameter of the mounting duct 110 is only slightly larger than the outer diameter of the negative pressure hose 56, whereby centering of the negative pressure hose 56 in the mounting duct 110 is achieved. In the third section S3, which also serves for positioning, the inner diameter of the mounting duct 110 is smaller than the outer diameter of the negative pressure hose 56. Thereby, the negative pressure hose 56 is shifted into the mounting duct 110 until it stops in the third section S3, whereby a correct axial positioning is ensured. It is understood that the fitting 54 of the suction cup part 58 can be analogously formed.

The parameter values indicated in the documents for the definition of process and measurement conditions for the characterization of specific characteristics of the inventive subject matter are to be considered as encompassed by the scope of the invention also within the scope of deviations— for example due to DIN tolerances and the like.

LIST OF REFERENCE CHARACTERS

10 Patient interface system
12 patient interface
14 patient interface holder
16 holding device
18 guiding device
20 second positioning device
22 connection device
24 camera system
26 illumination device
28 contact body
30 first positioning device
32 lighting means
34 connection cable
36 negative pressure hose
38 channel
40 window
42 interface body
44 holder
45 fitting
46 filter element
47 connector
48 mounting opening
50 collecting container
52 mounting opening
54 fitting
56 negative pressure hose
58 suction cup part
60 fluid-conducting device
62 suction duct
64 suction opening
66 cavity
68 teeth
70 mounting ribs
72a engaging surface
72b engaging surface
72c engaging surface
72a' engaging surface
72b' engaging surface
72c' engaging surface
74a ramp
74b ramp
76a engaging body
76b engaging body
76c engaging body
76a' spring-loaded engaging body
76b' spring-loaded engaging body
76c' spring-loaded engaging body
76d' spring-loaded engaging body 78 collar
80a assembly
80b assembly
80c assembly
82 engaging device
84 springs
86 housing
88 screws
90 bracket
100 collar
102 edge
104 lip
106 support surface
108 ribs
110 mounting duct
P optical path
K coupling path
L laser radiation
F spring force

What is claimed is:

1. A patient interface system for positioning a patient's eye relative to a laser device for laser surgery, comprising:
a patient interface for coupling to the patient's eye; and
a patient interface holder for arranging the patient interface on the laser device, wherein
the patient interface comprises a first positioning device for abutting the patient interface on the patient's eye and a second positioning device for positioning the patient interface relative to the patient interface holder, the second positioning device having collars,
the patient interface holder includes a holding device with two opposing, groove-shaped guiding devices along which the collars of the second positioning device of the patient interface are forcibly guided and slidable for coupling and decoupling, along a linear coupling path, the patient interface and the patient interface holder, the linear coupling path being substantially perpendicular to a direction of an intended laser radiation of the laser device through the patient interface system,
the patient interface holder comprises a suction duct connectable to a suction device, the suction duct of the patient interface holder including a male connector,
the patient interface comprises a fluid-conducting device including a female fitting that automatically connects to the male connector of the suction duct of the patient interface holder, when the second positioning device of the patient interface is coupled within the holding device of the patient interface holder, to form a fluid path therethrough, and
the fluid path fluidically couples the suction duct to a suction opening of the patient interface in a region of the first positioning device, to hold the first positioning device in abutment on the patient's eye by a relative negative pressure generated by means of the suction device.

2. The patient interface system according to claim 1, wherein the female fitting comprises an inner cone, in which a corresponding outer cone of the male connector is arranged in a coupled state.

3. The patient interface system according to claim 2, wherein the outer cone and/or the inner cone have a contact angle between 8° and 20° according to amount.

4. The patient interface system according to claim 1, wherein the male connector is formed angled and/or arranged in a groove of the patient interface holder and/or applied with force by a spring—loaded engaging element.

5. The patient interface system according to claim 1, wherein the fluid-conducting device of the patient interface includes at least one filter element.

6. The patient interface system according to claim 5, wherein the fluid-conducting device of the patient interface includes at least one collecting container, and the at least one filter element is arranged in a mounting opening of the at least one collecting container.

7. The patient interface system according to claim 1, wherein the fluid-conducting device of the patient interface includes at least one collecting container.

8. The patient interface system according to claim 7, wherein the at least one collecting container is inserted in a corresponding mounting opening of the patient interface and/or that the at least one collecting container has a volume of at least 80 mm$^3$.

9. The patient interface system according to claim 1, wherein the fluid-conducting device includes a negative pressure hose.

10. The patient interface system according to claim 9, wherein the fluid-conducting device of the patient interface includes at least one collecting container, and the at least one collecting container includes a fitting in which a first end region of the negative pressure hose is arranged.

11. The patient interface system according to claim 10, wherein the fluid-conducting device includes a fitting, in which a second end region of the negative pressure hose is arranged and which opens into the suction opening.

12. The patient interface system according to claim 10, wherein at least one fitting comprises a mounting duct, in which the negative pressure hose is arranged in certain areas, wherein the mounting duct has an inner diameter continuously and/or gradually decreasing at least in certain areas along a mounting direction starting from an introduction opening, the inner diameter of which at least corresponds to an outer diameter of the negative pressure hose.

13. A method for coupling a patient interface of a patient interface system according to claim 1 to a patient interface holder of the patient interface system, in which the patient interface is moved relative to the patient interface holder, until the male connector of the suction duct of the patient interface holder and the female connector of the fluid-conducting device of the patient interface are fluidically coupled and commonly form a fluid path, which fluidically couples the suction duct to the suction opening of the patient interface in the region of the first positioning device to hold the first positioning device in abutment on the patient's eye by a relative negative pressure generated by means of the suction device.

14. The patient interface system according to claim 1, wherein the patient interface is configured to be plugged into the holding device of the patient interface holder, via engagement of the collars of the second positioning device and the two opposing, groove-shaped guiding devices, in a drawer-like manner for coupling and decoupling.

* * * * *